(12) United States Patent
Call

(10) Patent No.: US 6,204,505 B1
(45) Date of Patent: Mar. 20, 2001

(54) SURGICAL PROBE APPARATUS AND SYSTEM

(75) Inventor: John D. Call, Columbus, OH (US)

(73) Assignee: Neoprobe Corporation, Dublin, OH (US)

( * ) Notice: Subject to any disclaimer, the term of this patent is extended or adjusted under 35 U.S.C. 154(b) by 0 days.

(21) Appl. No.: 09/167,643

(22) Filed: Oct. 6, 1998

(51) Int. Cl.[7] .................................................. G01T 1/161
(52) U.S. Cl. .............................. 250/370.01; 250/370.13
(58) Field of Search ........................... 250/370.13, 370.01

(56) References Cited

U.S. PATENT DOCUMENTS

| | | |
|---|---|---|
| 4,782,840 * | 11/1988 | Martin, Jr. et al. . |
| 4,801,803 | 1/1989 | Denen et al. . |
| 4,889,991 | 12/1989 | Ramsey et al. . |
| 4,893,013 | 1/1990 | Denen et al. . |
| 5,070,878 | 12/1991 | Denen . |
| 5,151,598 | 9/1992 | Denen . |
| 5,429,133 * | 7/1995 | Thurston et al. ................ 600/436 |
| 5,441,050 * | 8/1995 | Thurston et al. . |
| 5,475,219 | 12/1995 | Olson . |
| 5,482,040 | 1/1996 | Martin, Jr. . |
| 5,732,704 | 3/1998 | Thurston et al. . |
| 5,857,463 * | 1/1999 | Thurston et al. ................ 600/436 |
| 5,987,350 * | 11/1999 | Thurston ........................... 600/436 |

OTHER PUBLICATIONS

Butler, et al., "Cd$_x$ 2n$_x$TeGamma Ray Detectors, "Ieee Transactions or Nuclear Science, Santa Fe, N. Mex.,1991.

Morton, et al., "Technical Details of IntraOperative Lymphatic Mapping For Early State Melanoma," *Arch. Surg.*1992,127: 392–399.

Doty, et al., "Properties of Cadmium Zinc Telluride Grown by a High Pressure Bridgeman Method," *J.Vac.Sci.Techrol*, vol. B10 Jun./Jul., 1992.

Butler, et al.,"Recent Developments in Cd Zn Tr Gamma Ray Detector Technology, "Proceedings of the International Symposium of the SPIE, Santa Fe, N.Mex. Jul. 1992.

Uren, et al., "Lymphoscintigraphy in High Risk Melanoma of the Trunk: Predicting Draining Node Groups, Defining Lymphatic Channels and Locating the Sentinel Node." *J.Nuel Med.*1993; 34:1435–1440.

Giuliano, et al., "Lymphatic Mapping and Sentinel Lymphadenectomy For Breast Cancer, " *Annals of Surgery*, vol. 220, No. 3: 391–401, 1994 J. B. Lippincott Company.

Greenson, et al., Identification of Occult Micrometastases in Pericolic Lymph Nodes of Dukes' B Colorectal Cancer Patents Using Mancloral Antibodies Against CytoKeratin and CC49,: *Cancer*1994; 73: 563–569.

(List continued on next page.)

*Primary Examiner*—Constantine Hannaher
(74) *Attorney, Agent, or Firm*—Mueller and Smith LPA

(57) ABSTRACT

A surgical system wherein a two component hand-held probe is provided. The probe includes a sterilizable and reusable detector portion formed principally of metal in combination with a disposable handle and cable combination. Formed principally of metal components, the detector assembly includes a crystal receiver within which a detector crystal is retained in compression by an annular metal ring assembly having thin inwardly depending tines which contact the crystal forward surface and additionally apply the electrical ground thereto. An access channel rigidly supports bias and signal carrying electrical leads through a crystal mount to a rearward face thereof. The rearward face rigidly supports the forward stage of a preamplifier. In one embodiment a rigid polymeric crystal mount is employed. Particularly for this embodiment, a cup-shaped, shield containing window assembly is utilized.

37 Claims, 10 Drawing Sheets

OTHER PUBLICATIONS

Bertsch, et al., "Radioimmunoguided Surgery System Improves Survival For Patients with Recurrent Colorectal Cancer," *Surgery* 1995; 118: 634–639.

Arnold, et al., "Radioimmunoguided Surgery in Primary Colorectal Carcinoma: An Intraoperative Diagnostic Tool and Adjuvant to Traditional Staging" *American J. Surg* 1995; 179: 315–318.

Schneebaum, et al., The Significance of Intraoperative Periportal Lymph Node Metastasis Identification in Patients with Colorectal Carcinoma: *Cancer* 1995; 75: 2809–2817.

Cote, et al., Intraoperative Detection of Occult Colon Cancer Micrometasis Using $^{125}$–Radiolabeled Monoclona/Antibody CC49, *Cancer* 1996; 77: 613–620.

* cited by examiner

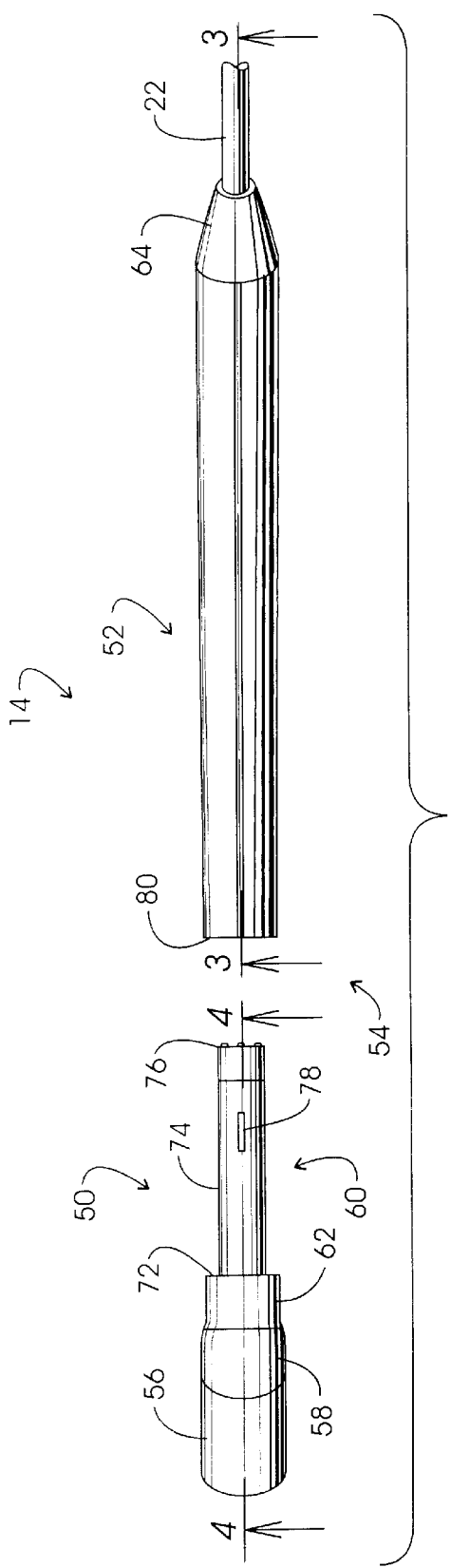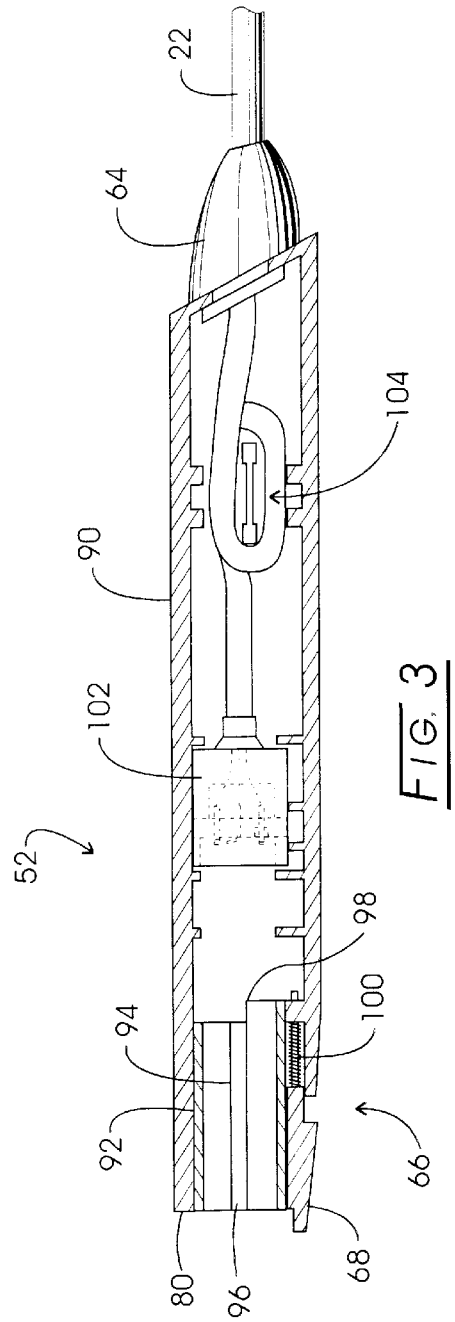
FIG. 2
FIG. 3

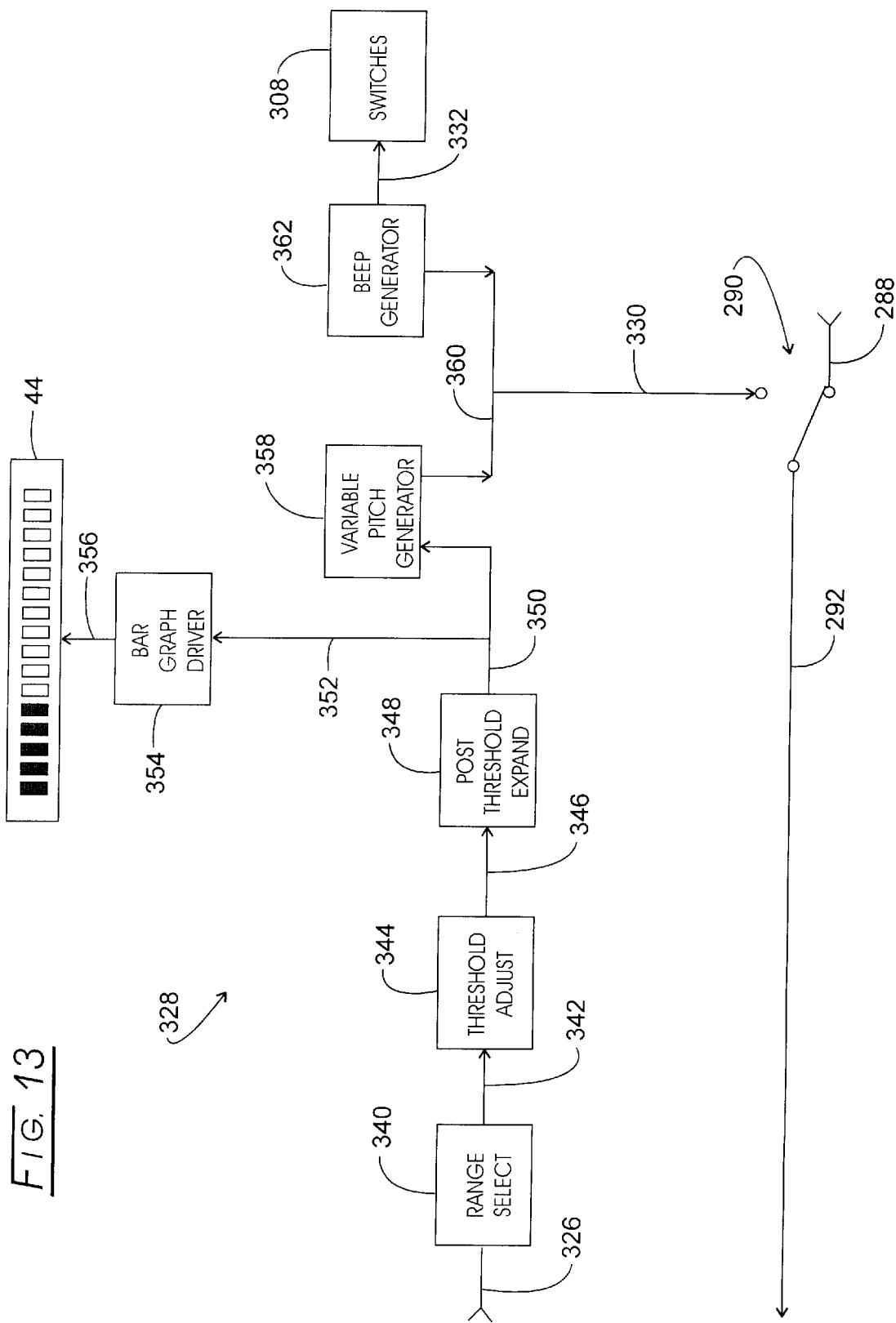

SURGICAL PROBE APPARATUS AND SYSTEM

CROSS-REFERENCE TO RELATED APPLICATIONS

STATEMENT REGARDING FEDERALLY SPONSORED RESEARCH

Not applicable.

BACKGROUND OF THE INVENTION

Current and historical procedures for treatment of colon and rectal cancer generally have been based upon the natural history of tumor spread, and thence, upon operative and non-operative options available to the practitioner. Operative options generally have looked to the physical identification and surgical resection of tumor. A variety of techniques have been brought to bear in the art with the purpose of aiding the surgeon in detecting and localizing neoplastic tissue as part of this surgical procedure. ("Neoplastic tissue," for the present purposes, often is referred to as cancerous tissue, though malignant tumor and malignant tumor cells also are found in the terminology of the art. The term "neoplastic tissue" includes all of these.) A substantial amount of the effort which has been expended in seeking to aid the surgeon in the process of locating neoplastic tissue has been concerned with the utilization of radiolabeled antibody. For example, one technique includes the scintillation scanning of patients who have been injected with relatively high energy, e.g. $^{131}$I labeled antibodies. Such photoscanning scintigrams are difficult to interpret because of blood pool background radioactivity. Computer subtraction of radioactive blood pool agents and the use of two labeled antibodies (one specific for the tumor and one nonspecific) have been attempted in an effort to enhance imaging. Nevertheless, such techniques have been found to provide little, if any, useful information to the surgeon, especially over and above the CAT scan, magnetic resonance imaging, and like traditional techniques. Typically, large tumor is readily located by the surgeon by visualization at the operating theater, and, in particular, through palpation, i.e. the feel of tumor as opposed to that of normal tissue. To achieve operative success, however, it is necessary for the surgeon to somehow locate "occult" tumor, i.e. tumor which cannot be found by the conventional surgical procedures of sight and feel. Failure to locate and remove such occult tumor generally will result in the continued growth of cancer in the patient, a condition often referred to as "recurrent" cancer. In general, conventional diagnostic techniques such as, for example, use of the classic gamma camera and the like, fail to find or locate occult tumor. As tumor sites become smaller, the radionuclide concentrations at a given site will tend to be lost, from an imaging standpoint, in the background where blood pool radiation necessarily is present in the patient.

In 1984, Martin, M. D., and Thurston, Ph.D., introduced a much improved method for locating, differentiating, and removing neoplasms. Such technique uses a radiolabeled antibody and a portable radiation detection probe which the surgeon may use intraoperatively in order to detect sites of radioactivity. Because of the proximity of the detection probe to the labeled antibody, the faint radiation emanating from occult sites becomes detectable, for example, in part because of the inherent application of the approximate inverse square law of radiation propagation. The procedure now is known as radioimmunoguided surgery (RIGS®) (RIGS being a registered trademark of Neoprobe Corporation of Dublin, Ohio). The RIGS system for surgery additionally is successful because of a recognition that tumor detection should be delayed until the blood pool background of the circulating radiolabeled antibody has had an opportunity to be cleared from the body. As a consequence, the photon emissions or radiation emitted at minute tumors, compared to surrounding tissue, becomes detectable in view of the proximity of the probe device to it. Fortuitously, the radiolabeled antibody is capable of remaining bound to or associated with neoplastic tissue for extended periods of time with the radio tag still bound thereto. Moreover, even though the accretion of radioactivity at the tumor site decreases over time, the blood pool background and surrounding tissue (relative to the tumor sites) decrease at a much greater rate so that the radioactive sites can be determined readily utilizing a hand-held probe positioned in close proximity with the tissue under investigation. The seminal patent concerned with the RIGS procedure is U.S. Pat. No. 4,782,840 by Martin, Jr. and Thurston, entitled "Method for Locating, Differentiating, and Removing Neoplasms," issued Nov. 8, 1988, and assigned in common herewith, the disclosure of which is expressly incorporated herein by reference.

The important advances achieved through radioimmunoguided-surgery have been reported. See in this regard, the following publications:

(1) "Radioimmunoguided Surgery System Improves Survival for Patients with Recurrent Colorectal Cancer" Bertsch, et al., *Surgery* 1995; 118: 634–639.

(2) "Radioimmunoguided Surgery in Primary Colorectal Carcinoma: An Intraoperative Prognostic Tool and Adjuvant to Traditional Staging," Arnold, et al., *American J. Surg.* 1995; 179: 315–318.

(3) "The Significance of Intraoperative Periportal Lymph Node Metastasis Identification in Patients with Colorectal Carcinoma," Schneebaum, et al., *Cancer* 1995; 75: 2809–2817.

(4) "Identification of Occult Micrometastases in Pericolic Lymph Nodes of Dukes' B Colorectal Cancer Patients Using Monoclonal Antibodies against Cytokeratin and CC49," Greenson, et al., *Cancer* 1994; 73: 563–569.

(5) "Intraoperative Detection of Occult Colon Cancer Micrometastases Using $^{125}$I-Radiolabeled Monoclonal Antibody CC49," Cote, et al., *Cancer* 1996; 77: 613–620.

The radioimmunoguided surgical system instrumentation is comprised generally of two basic components, a hand-held probe, as described above, which is in electrical communication via a flexible cable with a control console. This control console is located within the operating room facility but out of the sterile field, while the hand-held probe and forward portions of its associated cable are located within that field. The hand-held radiation detecting probe is relatively small and performs in conjunction with a cadmium-zinc-telluride detector or crystal.

The hand-held probe and preamplification electronics mounted within it in support of the cadmium-zinc-telluride crystal have been the subject of extensive scientific development. Cadmium-zinc-telluride crystals are somewhat fragile and exhibit piezoelectric properties which, without rigorous accommodation, will produce deleterious noise phenomena and the like. Further, the crystal and its operatively associated preamplification function are called upon to detect necessarily very faint radiation. In this regard, only a very small amount of radioactive locator will be associated with minute, occult tumor. Thus, radiation emission count rates measured with the RIGS system are relatively low.

Research activity concerning the above operational criteria is reflected in the following U.S. patents.

U.S. Pat. No. 4,801,803 by Denen, Thurston and Ramsey, entitled "Detector and Localizer for Low Energy Radiation Emissions," issued Jan. 31, 1989.

U.S. Pat. No. 4,893,013 by Denen, Thurston and Ramsey, entitled "Detector and Localizer for Low Energy Radiation Emissions," issued Jan. 9, 1990.

U.S. Pat. No. 5,070,878 by Denen, entitled "Detector and Localizer for Low Energy Radiation Emissions," issued Dec. 10, 1991.

U.S. Pat. No. 5,151,598 by Denen, entitled "Detector and Localizer for Low Energy Radiation Emissions," issued Sep. 29, 1992.

To derive data representing the presence or absence of occult tumor, a microprocessor-driven complex system of analysis continuously works to statistically evaluate validated counts or gamma strikes to aurally apprise the surgeon of the presence or absence of occult neoplastic tissue. An algorithm under which the noted evaluation takes place is described in U.S. Pat. No. 4,889,991 by Ramsey and Thurston, entitled "Gamma Radiation Detector with Enhanced Signal Treatment," issued Dec. 26, 1989.

The RIGS system, not only having demonstrated its value in locating occult neoplastic tissue, also substantially aids the surgeon in determining the proper staging of the patient in accordance with the extent and severity of the disease. Such staging aids in determining the appropriate post-surgical treatment of patients. In this regard, an effective staging technique utilizing the RIGS system has been described wherein an R Number is determined in accordance with the formula:

$$R\ Number=(n_1 \times E_1)_1+(n_2 \times E_2)_2+(n_3 \times E_3)_3+(n_4 \times E_4)_4$$

wherein each subscript 1–4 represents an anatomic zone, staging of the patient being based upon the R Number determination. See generally, U.S. Pat. No. 5,482,040 by Martin, Jr., entitled "Biostaging of Adenocarcinomas Utilizing Radiolabeled Tumor-Associated Glycoprotein Antibodies," issued Jan. 9, 1996.

Cadmium telluride-based crystals, when employed in conjunction with the RIGS system perform admirably. Advantageously, higher purity levels for the compound crystals are not mandated in order to generate highly acceptable count-based outputs within an energy region of interest. Such performance, typically, is evaluated in conjunction with a multi-channel analyzer (MCA) relating counts with energy levels of interest. Where a sharp photopeak at the energy level of interest occurs which, in turn, is well spaced from regions of an MCA curve representing electrical noise, Compton scattering or the like, then windowing or thresholding out of such noise is a straightforward procedure. Cadmium telluride-based crystals achieve this excellent performance, inter alia, because they are used in conjunction with the radionuclide $^{125}$I which exhibits relatively low gamma energy (27–35 Kev). By contrast, the commonly employed $^{131}$I exhibits gamma energy of 360 Kev. The cadmium-zinc-telluride crystals employed with the RIGS system are, for the purposes of the instant discussion, considered to be "thin," i.e. having a thickness, d, of 2 mm. With the RIGS system, upon the occurrence of a photon event, a generation of carrier pairs generally will occur in a manner wherein holes are trapped at the grounded front face of the crystal. From that position they are immediately collected by the initial integration stage of a signal treatment system. The carrier electrons, traveling at a velocity which is about twelve times greater than the rate of hole migration, all move essentially the same distance, such that, even if they are trapped, they are trapped to the same degree, and the result is an excellently performing crystal detection system.

Over the recent past, practitioners have been desirous of utilizing instrumentation similar to the RIGS system in conjunction with higher energy radionuclides. In particular, a call has been made for a cadmium telluride-based hand-held probe device which is operable in conjunction with the use of the radionuclide Technetium 99-m. The latter radionuclide exhibits a gamma energy level of, for example, 140 KeV. That value is somewhat excessive for the cadmium-telluride crystal architecture employed with the RIGS system. However, utilization of a hand-held probe with higher energy nuclides for the purpose of lymph system tracking is achieving importance.

The involvement of the lymph system in tumor metastasis has been the subject of extensive investigation and is well established. Lymphatic systems are present as widely dispersed tissues, fluids, and cells concerned in a variety of interrelated functions of the mammalian body including the circulation and modification of tissue fluid formed in the capillary beds, and the removal by mononuclear phagocytes of cell debris and foreign matter. The lymphatic system is importantly involved in participation with the blood vascular system in developing the immune response of the lymphocytes and other cells. Lymph flows within the system as a consequence of a variety of perceived mechanisms of organ and tissue dynamics. For certain cancers, metastasis, occurring in consequence of lymph drainage, will result in an initial location or positioning of neoplastic cells at certain lymph nodes typically deemed "regional nodes" within a pertinent lymph drainage basin. Some cancers, for example, melanomas, have been observed to exhibit variability in lymphatic drainage patterns emanating from different portions of the body. Other cancers, such as those encountered in the breast, will evidence somewhat more predictable nodal involvement. In designing forms of cancer disease management, therefore, efforts are directed to the identification of affected lymph nodes. For melanomas, it has been a more recent practice to identify the pertinent drainage basin or regional nodes along with an evaluation of the extent of lymph involvement with micrometastasis. A pre-surgical step undertaken in about 20% of investigational procedures concerning melanomas looks to the carrying out of a gamma camera generated form of lymphoscintigraphy which gives the clinician a gross two-dimensionally limited image, generally showing the tumor site injection of sulfur colloid labeled with Technetium 99-m ($^{99m}$Tc) and, spaced therefrom, a region of radioactivity at the pertinent regional lymph nodes. The latter information at least confirms the path of drainage and the location of the proper drainage basin. Regional nodes then are removed and submitted for pathology evaluation.

For cancers, such as breast cancer, the sites of lymph node involvement are commonly encountered at axillary, internal mammary, and supraclavicular lymph node regions. Of these, the axillary lymph node region is the principal site of regional metastasis from carcinoma of the breast, and approximately 40% of patients have evidence of spread to the axillary nodes. In early approaches to the disease, these axillary nodes were removed as a form of therapy. Presently, however, their positive involvement, or lack thereof, has become the subject of diagnostics, as opposed to therapy. In this regard, the combination of the presence and extent of metastasis to the axilla represents the single most important prognostic factor for the management of patients with breast cancer. See generally "Cancer, Principles and Practice of Oncology," vol. 1, 4th ed., DeVita, Jr., et al., chapter 40, Harris, et al., J.P. Lippincott Co., Philadephia, Pa. (1993).

The axilla is a triangular region bounded by the axillary vein superiorly, the latissimus dorsi laterally, and the serratus anterior medially. With more current diagnostic procedures, essentially all axillary nodes at the axilla assumed to represent the drainage basin are removed during surgery for analysis. In general, somewhere between 10 and 30 nodes will be removed in the course of dissection with, of course, the attendant risks. In this regard, these nodes are generally surrounded by investment or fatty tissue and visualization of them necessarily is limited. Such dissection will pose risks of cutting the long thoracic nerve, the thoracic-dorsal nerve, the nerve to the pectoralis major or the axillary vein. Morbidity may occur in some cases due to regional node removal, and patients are known to frequently discuss a numbing of the arm region following the procedure.

While this form of somewhat radical axillary lymph node dissection has been the conventional approach to determining nodal metastatic involvement, more recent data suggests that less radical axillary node evaluation procedures may generate equivalent information for staging and patient management, but with far more limited dissection and resultant trauma, as discussed below.

Patient management for staging purposes for the case of cutaneous melanoma is highly predicated upon determinations of lymph involvement. A number of factors are involved in the prognosis of the disease, including, inter alia, location, tumor thickness, level of invasion, growth patterns, and, of particular importance, the identification of regional node metastatic involvement. Generally, surgical excision of metastatic nodes within the drainage basin of a lesion has been considered the only effective treatment for cure or disease control. Some investigators have preferred to excise only clinically demonstrable metastatic nodes associated with the lesion, while others have chosen to excise the nodes even where they may appear normal because of the risk of the presence of occult (clinically undetectable) metastasis. A substantial dialog has been carried on by investigators as to whether or not elective lymph node dissection, or lymphadenectomy, is an appropriate therapy. Elective lymphodenectomy has the major advantage of treating a nodal metastasis at a relatively early stage in its natural history when the tumor burden is low. On the other hand, such an approach may subject patients to surgery which would otherwise have been unnecessary. In particular, where patients exhibit a clinical Stage I level of the disease, there will be no nodal metastasis present, and no benefit then can be realized from regional lymphadenectomy.

Morton, et al., undertook an investigation of a procedure designed to identify that lymph node nearest the site of a melanoma and within the pertinent lymph drainage basin. Such a node, being on the most direct drainage pathway will present the most likely site of early metastasis and is referred to as the "sentinel node." Thus, by carrying out only a limited dissection, specific to this node and performing pathologic analysis of it, staging can be achieved without at least initial resort to more radical lymphadenectomy. With the approach, once the drainage basin from a lesion is identified, for example, by lymphoscintigraphy, an intraoperative mapping of the cutaneous lymphatics with vital dye is carried out at the time of surgical removal of the primary lesion. The vital dye, for example of blue color, is injected at the site of the lesion and tracked by blunt dissection until the sentinel node is reached. That node is now exclusively of blue color and readily identified. Thus, the sentinel draining lymph node of each primary melanoma is isolated and removed. By examining the sentinel nodes, for example by frozen section using routine hematoxylin-eosin histopathological techniques, as well as rapid immunohistochemical techniques, only those patients who have evidence of micrometastasis in the sentinel draining node are subject to subsequent lymphodenectomy. See generally, Morton D., Wen D -R, Wong J., et al. "Technical Details of Intraoperative Lymphatic Mapping for Early Stage Melanoma," *Arch. Surg.* 1992: 127:392–399; and R. F. Uren, et. al, "Lymphoscintigraphy in High-Risk Melanoma of the Trunk: Predicting Draining Node Groups, Defining Lymphatic Channels and Locating the Sentinel Node," *J. Nucl Med* 1993; 34:1435–1440.

The approach of Morton, et al., also has been undertaken to moderate the otherwise somewhat radical axillary lymph node dissection common in staging breast cancer. Through the utilization of the noted vital dyes, in conjunction with the lymph drainage system from primary breast tumor, less radical sentinel node based procedures may result in adequate axillary staging and regional control. With the procedure, in general, a vital blue dye is injected into the breast mass and surrounding breast parenchyma. Following a relatively short interval, a transverse incision is made just below the hair bearing region of the axilla. Blunt dissection is performed until a lymphatic tract or duct leading to a blue stained node is identified. The lymph duct, having a blue color, provides a guide path leading to the location of the most proximal lymph node and thus the sentinel node. This sentinel node is excised and evaluated. While the procedure calls for considerable surgical experience and talent associated with the delicate task of following the blue duct (a ruptured dye-carrying duct can be problematic), the ability to identify a tumor-free sentinel lymph node will enable the surgeon to accurately stage metastasis-free breast cancer patients without subjecting them to the risks of radical dissection. The approach may also improve histologic staging by enabling the pathologist to focus on fewer lymph nodes. See generally Guiliano, A. E.; Kirgan, B. M.; Guenther, J. M.; and Morton, D. L., "Lymphatic Mapping and Sentinel Lymphadenectomy for Breast Cancer," *Annals of Surgery*, vol. 220, no. 3: 391–401, 1994, J.B. Lippincott Company.

As a replacement for or an adjunct to the tracking of portions of the lymph system to locate a sentinel lymph node, practitioners have injected the noted sulfur colloid labeled with $^{99m}$Tc technician at the site of the lesion. Then, employing a hand-held radiation detecting probe, migration of the injectate along the lymph ducts to the sentinel node is carried out. Thurston, et. al, in U.S. Pat. No. 5,732,704 entitled "Radiation Based Method for Locating and Differentiating Sentinel Nodes," issued Mar. 31, 1998, describe an improved technique for thus tracking a lymph duct and for utilizing a thresholding procedure three-dimensionally finding a radiolabeled sentinel lymph node with a hand-held probe. An improved apparatus and system for carrying out this procedure is described by Thurston and Olson in an application for U.S. patent Ser. No. 08/543,032 filed Oct. 13, 1995 and entitled: "Remotely Controlled Apparatus and System for Tracking and Locating a Source of Photo Emissions."

The performance of cadmium-telluride based hand-held probes, when used with radionuclides of higher energy such as $^{99m}$Tc, has been the subject of investigation. Thurston, in application for U.S. patent Ser. No. 09/167,008 entitled "Radiation Probe With Compound Semiconductor Crystal Performing In A Trapping-Dependent Operational Mode," filed Oct. 6, 1998, describes a probe architecture and operational approach wherein good count efficiency and very good windowing of background is achieved. With the approach, an operational mode is employed wherein a trapping of substantially all carriers occurs within the volume of the compound semiconductor. In general, this calls for the use of a thicker crystal in combination with relatively lower voltage biasing procedures. In addition to the development of such alternate operational modes, investigations continue to be addressed to techniques for the mounting and use of cadmium-telluride based crystals such that they are less prone to the generation of noise phenomenon resulting from movement-based use of the probes in the course of surgery and the like. Other investigations have looked to the practical aspects of clinical use of the probes. For example, the bending of transmission cable excessively may result in damage to the cable connectors as well as to the cable. To avoid these problems, cables with more elaborate structuring can be procured, but such cables are more expensive and do not eliminate the problems cause by induced strain and deterioration over extended use.

Cleaning and sterilization of the hand-held probes also has been the subject of investigation. After each use, contaminates and body fluids must be removed from the probe, transmission cable and the connector between the probe and the cable. To be able to remove all of the exterior particles and fluid, the probe surfaces must be smooth and free of cracks and recesses. Such a requirement necessarily increases the cost of manufacture. In addition, the connector, into which the transmission cable is inserted, has in the past consisted of a complex opening with a depth of up to ⅜ of an inch. This has proved a difficult region to clean.

Sterilization of instruments and equipment is essential in a surgical setting to kill pyogemic organisms, such as *staphylococcus aureus,* which are not killed by alcohol or other cleaning agents. There are currently a number of methods available for the sterilization of surgical instruments. One of the oldest and quickest ways of sterilizing surgical instruments is by the process of autoclaving. The instrument is placed under high pressure and the temperature is raised to around 140 degree Celsius. Such a process could not be used for probe devices of the past because of the thermal effects on the internal circuitry as well as crystal mounting components of the probe. As a result, most probes have been sterilized with ethylene oxide gas, EtO. This process is more time-consuming than autoclaving, often requiring twenty-four hours for completion. In addition, care must be taken in handling the gas because it is flammable, toxic and corrosive to certain types of plastic. Thurston, in application for U.S. Pat. No. 5,987,350 issued Nov. 16, 1999 and entitled "Surgical Probe Apparatus and System," describes a probe architecture wherein the probe component is formed of two parts. A forward component is sterilizable and reusable containing the cadmium-telluride based crystal and preamplification stage. This reusable and sterilizable device then is insertible within a handle and cable combination which is formed of plastic and is disposable.

BRIEF SUMMARY OF THE INVENTION

The present invention is addressed to a surgical probe apparatus and system having a detector assembly which is designed to very rigidly retain a semiconductor crystal without resort to adhesives, cushion layers or the like. Additionally, the crystal mounting structure is fashioned to rigidly secure bias leads contacting the rearward face of the crystal and to further rigidly support the associated integrator stage of a probe-contained preamplifier network. Those forward components of the preamplifier are mounted upon a circuit board, which, in turn, is rigidly received at a slot within a relatively massive crystal mount at its rearward face. The semiconductor crystal itself and bias signal carrying leads are constrained against movement by the crystal mount assembly. A forward cavity portion of the crystal mount assembly and an associated retainer engages the CdTe semiconductor crystal in compression. Integrally formed with the cavity portion of the crystal mount assembly is an access channel within which multi-strand bias and signal carrying leads are secured against movement and which extends through the crystal mount into immediate adjacency with the integrator stage of a preamplifier network. With such structuring, electrical noise evoked from varying capacitance phenomena are avoided. Additionally, piezoelectric generated noise phenomena at the crystal detector are avoided.

The forward portion of the crystal mount extends forwardly from its rigid attachment with handle associated components in cantilever fashion to, in turn, support the crystal detector. This entire mount forward portion with crystal is surmounted by a cup-shaped window assembly, which includes a radiation attenuating side shield, the interior surfaces of which are spaced from the crystal detector forward surface to define a forward gap and from the mount sides to form a side gap, thus providing an isolation of the forwardly extending mount structure. This mounting architecture may be provided with more conventional unitary hand-held probe structures, as well as with those of a variety utilizing a reusable, sterilizable detector assembly in combination with a disposable handle-cable assembly.

In one embodiment, the crystal mount of the crystal mount assembly is formed of an electrically insulative, polymeric material. With the inclusion of a polymeric crystal mount, varying capacitance induced noise is avoided, inasmuch as a substantial distance exists between the biased leads and grounded probe components structure. In this embodiment, the forward cavity of the crystal mount assembly, which retains the semiconductor crystal, is formed within the polymeric crystal mount.

In another embodiment, the crystal mounting assembly includes a metal crystal mount. The semiconductor crystal itself and bias signal carrying lead are constrained against movement by a rigid, polymeric crystal receiver, which in turn, is rigidly mounted within the metal crystal mount. In this embodiment, the forward cavity of the crystal mount assembly is formed by the polymeric crystal receiver, and integrally formed with the cavity portion of the receiver is an elongate rigid stem extending in a press-fit fashion through the access channel to rigidly retain the bias and signal carrying lead.

In a preferred embodiment, the detector crystal is retained in compression within the forward cavity portion of the crystal mount assembly by a retainer and grounding assembly having an electrically conductive annular ring. Formed with this ring are inwardly depending thin tines which abuttably engage the forward face of the crystal detector, retaining the crystal detector in compression and applying electrical ground. The ring further is formed having symmetrically disposed dogs which engage the metal crystal mount to retain the annular ring in position against the crystal mount and to assure the application of electrical ground to the crystals forward surface.

The crystal detector supporting components are formed principally of metal and polymeric materials in a fashion where the probe is amenable to more simplified repair procedures. Additionally, the metal components are specifically grounded to achieve highly effective circuit shielding. This metal structuring also permits a minimal spacing of the crystal forward surface from an associated radiation transmissive window while still maintaining an acoustical filtering gap between them.

In a further embodiment, the surgical system utilizes a reusable, sterilizable detector assembly in combination with a disposable combination of handle and flexible cable.

Other objects of the invention will, in part, be obvious and will, in part, appear hereinafter. The invention, accordingly, comprises the system possessing the construction, combination of elements and arrangement of parts which are exemplified in the following description.

For a fuller understanding of the nature and objects of the invention, reference should be had to the following detailed description taken in connection with the accompanying drawings.

BRIEF DESCRIPTION OF THE DRAWINGS

FIG. 2 is a top view of a probe instrument shown in FIG. 1 showing separately the forward and rearward components thereof;

FIG. 3 is a sectional view taken through the plane 3—3 in FIG. 2;

FIG. 13 is a block diagram showing variable pitch generator components of the system of the invention; and FIG. 14 is a stylized multi-channel analyzer plot showing counts versus gamma energy.

DETAILED DESCRIPTION OF THE INVENTION

Figure 1:
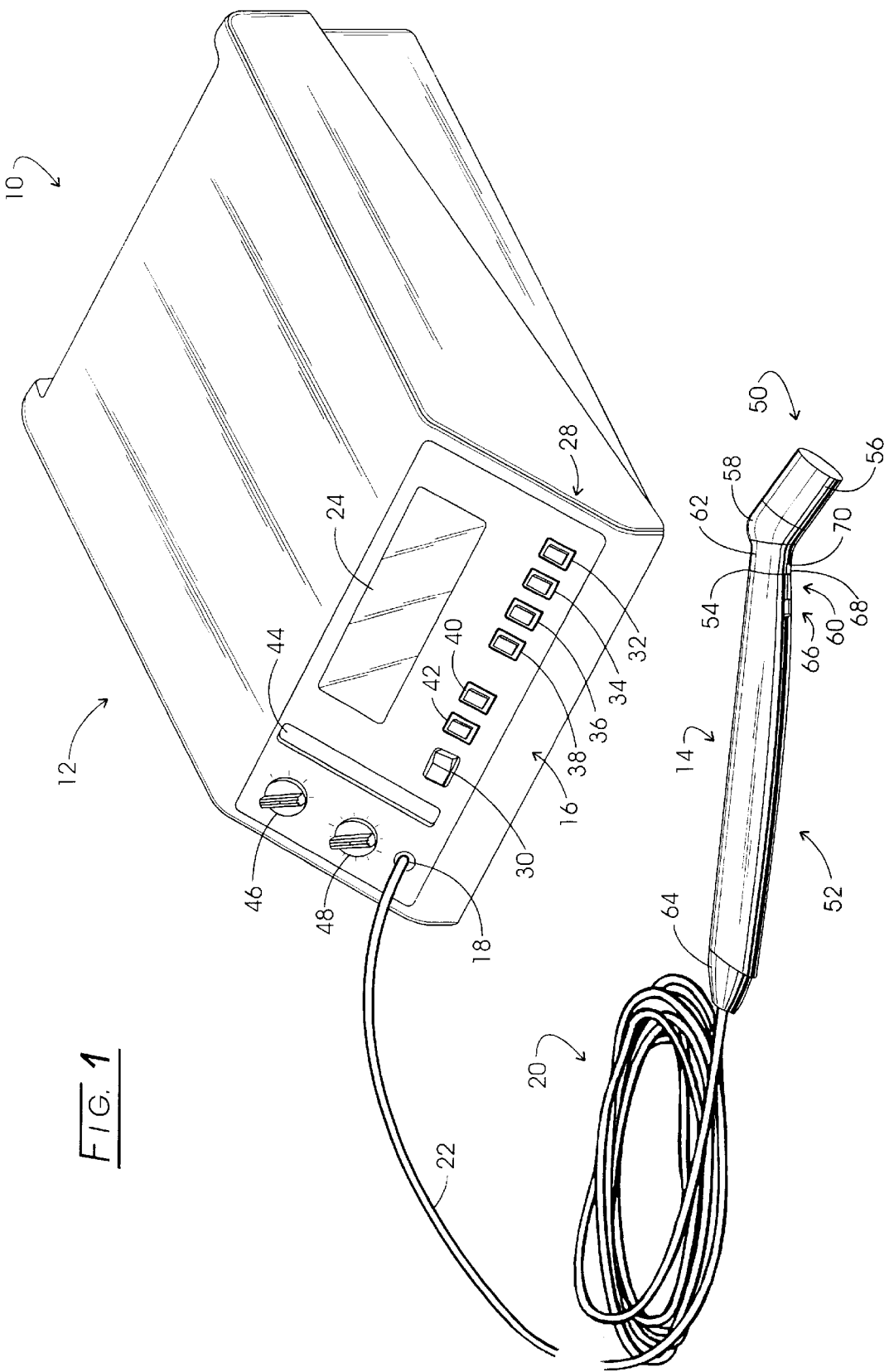
FIG. 1 is a pictorial representation of an embodiment of the system and apparatus of the invention.

Referring to FIG. 1, a radioimmunoguided system (RIGS™) incorporating the features of an initial embodiment of the invention is represented generally at 10. System 10 includes a control assembly or console 12 to which is coupled a probe or probe instrument represented generally at 14. The control console 12 is configured for both carrying out radioimmunoguided surgery and for tracking radiopharmaceuticals injected at the situs of the tumor to locate a lymph sentinel node. In the latter regard, the photon count evaluation, including lower threshold and upper limit windowing and discriminator functions of the RIGS system, is commonly utilized. Such a system is described, for example, in the above noted U.S. Pat. No. 4,801,803. The forward face 16 of console 12 includes a coupling or connector 18 which provides for electrical signal communication and power supply association with the probe instrument 14 via a transmission assembly represented generally at 20 which includes a flexible cable 22. This cable implementation of the transmission assembly is a preferred arrangement for such transmission functions, however, other approaches will occur to those skilled in the art. Forward face 16 of console 12 additionally carries a relatively large liquid crystal display (LCD) readout 24, as well as an array of push-type switches represented generally at 28. This array of switches 28 permits the microprocessor driven control assembly 12 to carry out an instructive or "user friendly" dialogue with the practitioner. In addition to a conventional on and off rocker switch 30, the switches provided at forwarded face 16 include such function selection switches as a count mode switch 32, a reset count switch 34, a background count or "squelch" switch 36, a sound control switch 38, and down and up incrementing switches shown respectively at 40 and 42.

Also mounted at the forward face 16 of console 12 are components dedicated to the lymph-tracking features of the system 10. In this regard, a linear, segmented LED array 44 is included for the purpose of providing a visual cueing aspect as to peak count rate level. A range selection switch is provided at 46. Switch 46 permits the practitioner to select any of five count ranges to achieve full-scale readouts. These ranges may, for example, be 0–100 counts per second; 20–1,000 counts per second; 50–2,500 counts per second; 100–7,500 counts per second; and 600–30,000 counts per second. Below the knob actuated range switch 46 is a knob actuated threshold control 48 which is used to provide a count rate threshold input. This input is a percentage valuation of any one of the count ranges established at switch 46. Such thresholding is a variation of the background count or "squelch" procedures carried out in connection with switches 34 and 36. In this regard, the function of reset count switch 34 is to derive a count value over a preset interval, for example, two seconds. The background count switch 36 is employed in conjunction with reset count switch 34 to develop a statistical count value based upon a measured background count rate. For example, in the RIGS procedure, the probe instrument 14 initially is positioned in the vicinity of the heart or aorta in order to obtain a blood pool background count rate. The interval during which this rate is determined is, for example, five seconds. The microprocessor-based control system of console 12 then calculates a statistically significant value, for example, a predetermined number of standard deviations of the basic background count rate to derive a statistically significant threshold radiation count rate level. This, for example, may be 3 sigma above the base count rate. The ranging procedure is referred to by surgeons as "squelching." Operating in conjunction with that threshold level in the RIGS procedure, the system 10 provides the surgeon with audible cues indicating that a high probability of tumor involvement is present at a location closely adjacent the position of the forward window of probe instrument 14. Because, for occult tumor, the probe instrument 14 performs approximately in conformance with the inverse square law of radiation propagation, it is important that the forward face of the detector crystal be as close to that occult tumor as possible. This has important ramifications upon the design of the forward components of the probe 14. The "squelching" procedure also may be utilized in conjunction with the detecting and locating of sentinel lymph nodes in connection with breast cancer or melanoma studies or procedures. However, with the system 10, a dedicated adjunct system is provided for that purpose. Positioned at the rear of the console 12 is a mode selection switch (not shown) which is manually actuated to either of two positions, one electing that the system 10 operate in its standard RIGS mode, and the other electing that the system 10 operate in conjunction with the adjunct system for carrying out sentinel node detection procedures and the like.

The probe 14 is formed of two complimentary components, a forward detector component represented generally at 50 within which are mounted a radiation responsive crystal and more particularly a cadmium-zinc-telluride crystal, along with a preliminary treatment circuit which will include a preamplifier integrator stage, as well as associated amplification stages. The detector component 50 is configured principally of metal components and, in a preferred embodiment, is heat sterilizable and further configured with very smooth surfaces to enhance its cleanability. These more expensive components then are permanent in nature in that the detector 50 is reusable over an extended period of time. Detector component 50 is removably insertable within a disposable handle component represented generally at 52. The juncture between the two components 50 and 52 is at a shoulder surface of component 50 and a contact surface of component 52 seen at interface line 54. Further observable in FIG. 1 is a cup-shaped window assembly 56, a detector forward support 58 and a detector rearward support represented generally at 60 and including a shoulder portion 62. The disposable handle component 52 is permanently attached to the flexible cable 22 and a cable relief assembly is shown at 64. Located forwardly on the handle component 52 is a latch assembly represented generally at 66 which is formed having an engaging component 68 spring biased for forward movement. In compliment with the engaging component 68, the detector rearward support shoulder portion includes a latching notch 70 extending inwardly from a shoulder surface at interface 54 and located for receiving the engaging component 68 when the detector assembly 50 is properly oriented upon handle 52.

Looking to FIG. 2, a top view of the probe 14 is revealed with a forward detector component 50 and disposable handle 52 being shown in spaced apart relationship. In the figure, the shoulder portion 62 of the detector rearward support 60 is shown extending to a shoulder surface 72 of annular configuration. Extending outwardly from that shoulder surface 72 is a cylindrical positioning shaft 74. Shaft 74 extends to an electrical terminal assembly 76. Also shown extending from the shaft 74 is a rectangular guide boss 78. Correspondingly, the disposable handle 52 is configured having a contact surface 80 which engages the shoulder surface 72 when the components 50 and 52 are joined to form the interface 54 (FIG. 1).

Looking to FIG. 3, a sectional view of the handle 52 is revealed. Handle 52 is formed having an outer plastic housing 90 of generally cylindrical shape. Forwardly mounted within housing 90 is a cylindrical retainer portion which extends forwardly and is coplanar with the contact surface 80. Retainer portion 92 defines and surmounts a receiving cavity 94 though which the positioning shaft 74 (FIG. 2) is inserted. The retainer portion 92 additionally includes two guideways, one of which is revealed at 96 intended for receiving a boss such as the orientation boss 78 shown in FIG. 2. Retainer portion 92 additionally is configured to provide stops, one of which is shown at 98, which function to limit the extent of rotation of the detector component 50 upon insertion of the positioning shaft 74 within receiving cavity 94. Seen in adjacency with the retainer portion 92 is the earlier noted latch assembly 66 including engaging component 68 and a spring 100 which functions to bias the engaging component 68 forwardly to the orientation shown. Mounted rearwardly from retainer portion 92 within the housing 90 is a combined electrical contact and sealing assembly 102 which receives, seals and makes appropriate contact with the electrical terminal assembly 76 of detector component 50. Cable 22 is seen to extend through relief 64 and thence is wrapped about a second relief 104, whereupon it is coupled to the electrical contact and sealing assembly 102. Within that assembly, the leads of cable 22 are connected with a circular array of discrete leaf contacts which make contact with the terminal assembly 76 when the shaft 74 is inserted within the handle 52. Handle 52 is described in detail in U.S. Pat. No. 5,987,350 (supra).

Figure 4:
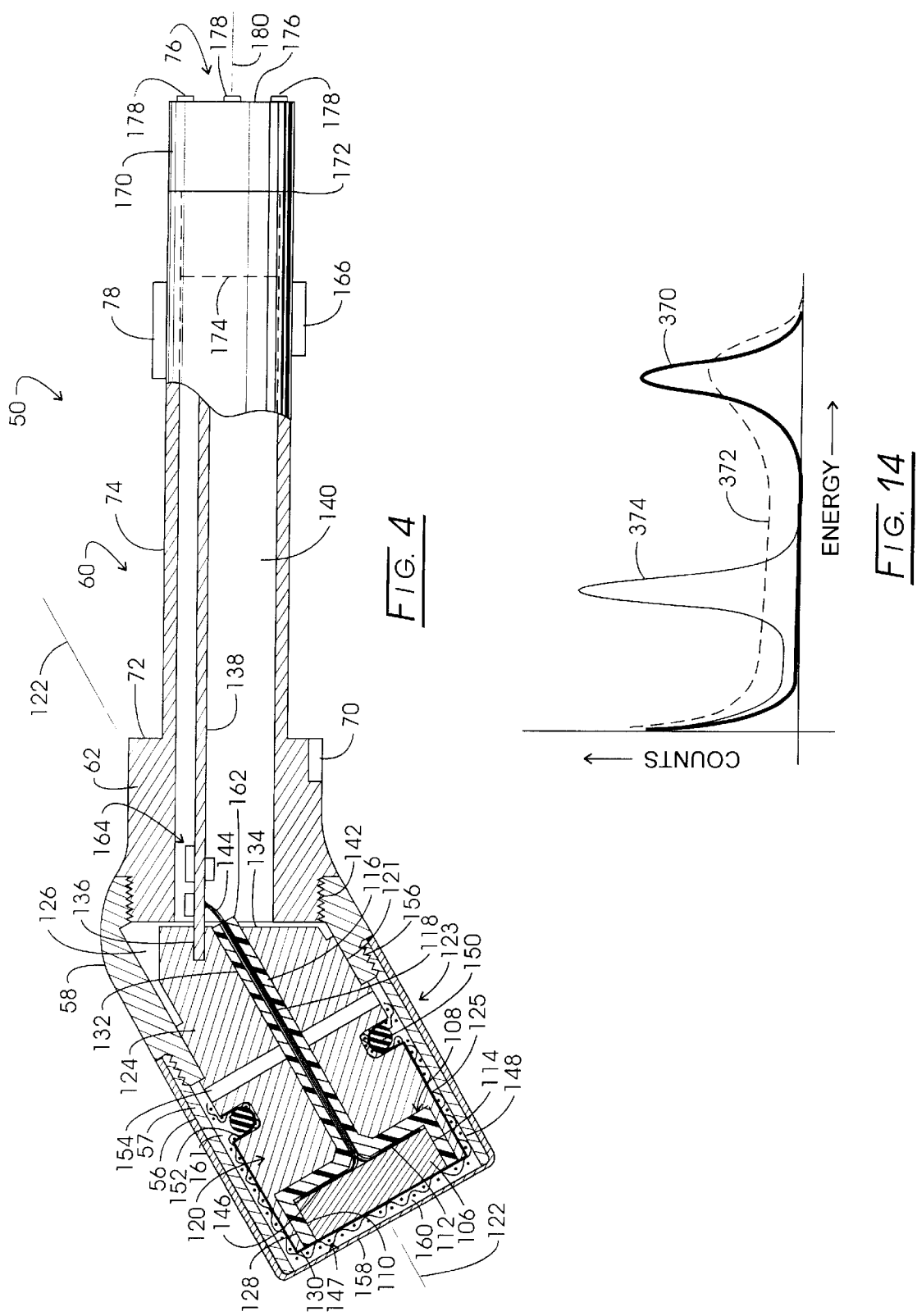
FIG. 4 is a sectional view taken through the plane 4—4 in FIG. 2.

Referring to FIG. 4, an initial embodiment for the detector component 50 is illustrated. In this embodiment, a cadmium-zinc-telluride crystal is utilized which is dimensioned both in forward looking surface area and in thickness for the purpose of carrying out the RIGS procedure, a procedure involving a relatively low level energy radionuclide. When so used with the RIGS system, upon the occurrence of a photon event, a generation of carrier pairs generally will take place in a manner wherein holes are trapped at the grounded front face of the crystal. From that position they are immediately collected by the initial integration stage of an associated signal treatment system. The carrier electrons, traveling at a velocity which is about twelve times greater than a possible rate of hole migration, all move essentially the same distance. Even if they are trapped, they are trapped to the same degree, and the result is an excellently performing crystal detection system.

Cadmium-telluride crystals may be alloyed and still are referred to as "cadmium telluride" or "CdTe" crystals for present purposes. A preferred cadmium-telluride crystal, as is described in commonly-assigned U.S. Pat. No. 5,441,050, issued Aug. 15, 1995, is CdTe material alloyed with zinc and is generally represented by the expression; $Cd_xZn_xTe$. In general, CdTe detecting crystals exhibit benefits such as operability at room temperature, high counting rates and small size. The proportioning of the Cd component and Zn component of the crystals may vary to provide an effective ratio selected to suit the particular requirements of the user. However, a lower limit or boundary for the proportion of zinc wherein x equals about 0.2 has been determined. Information concerning the alloyed crystals is provided in the following publications:

Butler, Lingren and Doty, "$Cd_{1-x}Zn_xTe$ Gamma Ray Detectors" IEEE Transactions on Nuclear Science, Santa Fe, N. Mex., 1991.

Butler, Doty and Lingren, "Recent Developments in CdZnTe Gamma Ray Detector Technology," Proceedings of the International Symposium of the SPIE, Santa Fe, N. Mex., July, 1992.

Doty, Butler, Schetziaa and Bowers, "Properties of Cadmium Zinc Telluride Grown by a High Pressure Bridgman Method," *J. Vac. Sci. Technol.,* Vol. B10, June/July, 1992.

To avoid the generation of what may be deemed "electrical noise" and noise which is evoked due to the piezoelectric nature of the crystals, a rigid form of mounting for not only the crystals but also the circuit components immediately associated with them becomes important. For example, any relative movement of circuit leads or components carrying a bias voltage with respect to surrounding ground will evoke a capacitance variance which may be manifested as an electrical noise signal. In FIG. 4, a cadmium-telluride crystal is shown at 106. The compound crystal 106 has a thickness of two millimeters and is seen to be positioned within a rigid, polymeric electrically insulated crystal receiver represented generally at 108. Receiver 108 is configured having a cylindrically shaped forwardly opening crystal receiving cavity 110 with a bottom surface 112 and an interior sidewall surface 114. Integrally formed with the receiver 108 is an elongate rigid stem 116 having a channel 118 extending therethrough.

Polymeric crystal receiver 108, in turn, is rigidly mounted to a crystal mount represented at 120. Crystal mount 120 is formed of a metal material attenuating radiation emission and will be formed, for example of tungsten, lead, brass or the like. The mount 120 has a generally cylindrical configuration and is seen to be disposed about a detector axis 122. The rearward portion 124 of mount 120 is mounted at a connection region 121 within the interior support cavity 126 of detector forward support 58. Connection is provided, for example, utilizing an electrically conductive epoxy material. Thus, the mount 120 is secure against any motion with respect to the forward support 58. Mount 120 is configured having a forward support portion 123 extending from the rearward portion and having a cylindrical outer surface 125. Forward portion 123 is further configured having a forwardly disposed mount cavity which opens forwardly and is symmetrically disposed about the detector axis 122. Cavity 128 extends to an annular mount cavity edge 130 and is seen to closely support the polymeric crystal retainer 108. Polymeric stem 116 is accommodated within an access channel 132 which extends from the bottom surface of the mount cavity 128 to the crystal mount rear face 134. Formed into that rear face 134 is a slot 136 which functions to rigidly support a printed circuit board 138. Printed circuit board 138 extends within an internal shaft cavity 140 of the detector rearward support 60. It may be observed that the shoulder portion 62 of the detector rearward support 60 is threadably engaged with the detector forward support 58 at 142. This provides a rigid coupling of relatively substantial size to assure that no relative movement will occur between the forward support 58 and rearward support 60. This feature also aids in both assembly and disassembly for probe manufacture and repair purposes. From connection with the bottom of circuit board 138, a plurality of positive bias carrying electrical wire strands formed as an insulated lead 144 extend through the channel 118 within stem 116 of the crystal receiver 108. These strands extend forwardly to be splayed or spread apart in spider-like fashion at 146 at the bottom surface 112 of crystal receiver 108. The lead 144 is rigidly secured within channel 118 and its strands 196 are retained in abutting contact with bottom surface 112 by the rear face of crystal 106. Preferably, no adhesives or cushioning devices are utilized in this mounting. Detector crystal 106 is compressably retained against the array of leads 146 by a retainer and grounding assembly 147 including a nylon web 148 which is stretched over the forward face of crystal 106 and retained in position by an elastomeric o-ring 150. O-ring 150 is seen to be nested with a portion of web 148 within an annular groove 152 extending about the surface 125 of crystal mount 120. Electrical ground is coupled to the rear face 134 of crystal mount 120 by a soldered connection with a ground pad (not shown) provided on circuit board 138. To apply electrical ground to the forward face of crystal 106, fine platinum wires (not shown) are embedded within the outer surface of crystal mount 120 and folded over the face of crystal 106. The nylon web 148 then retains the entire assembly compressably against bottom surface 112. This technique for compressably retaining the crystal 106 in position and asserting ground at the forward face of the crystal has been successfully employed with cadmium-telluride probes for a number of years. The initial use of the nylon web is described in U.S. Pat. No. 5,070,878 (supra). A drawback of the nylon web approach, however, is that the material is not heat sterilizable, for example using autoclave techniques. Extending across the crystal mount 120 is a pressure relief channel 154.

Covering the assembly of crystal 106, crystal receiver 108 and crystal mount 120 as well as the resilient nylon retainer 148 is the cup-shaped window assembly 56. Window assembly 56 is seen to be formed having a cylindrical, interiorally disposed side shield 57 formed of material attenuating radiation, such as tungsten. Shield 57 is threadably engaged with the forward portion of forward support 58 at a cylindrical threaded connector region 156, and facilitates both manufacture and subsequent repair procedures. Shield 57 buttresses and supports the aluminum component of the window assembly 56 which is thicker in dimension along the sides of crystal mount 120 and is made thinner at the forward face 158. No contact is made with any of the thus surrounded components, and, in particular, a forward gap 160 is defined between the forward face of crystal 106 and the inward surface of the forward looking portion 158 of window assembly 56. This gap 160 functions as an acoustic filter. Because of the noted approximate inverse square law based operation of the probe 14 with crystal 106, it is important that the gap be provided to accommodate the piezoelectric attributes of the crystal 106 but that it be of minimum dimension. A desirable spacing for gap 160 has been found to be about 0.015 inch.

The noted surrounding of internal components by the cup-shaped window assembly 56 also provides a cylindrical gap 161 between the cylindrical outer surface of 125 of crystal mount of 120 and the internal surface of the thicker side components of the window assembly 56. As a consequence, the relatively massive crystal mount 120 stands in cantilever fashion in surrounding space from a robust mounting with the detector forward support 58. Because of the electrically conductive connection of the assembly 56 with the portion 58 which, in turn, by virtue of its electrically conductive mounting of the specifically grounded mount 120, electrical ground coupling is made with the window assembly 56. In effect, a ground-to-ground association exists between the mutually facing interior surface of window assembly 56 and the surface 125 of mount 120. This same relationship exists between the thin window portion 158 and the grounded forward surface of crystal detector 106. Accordingly, in the event of some impact-induced movement into the window assembly 56, no capacitance variation induced electrical noise will be developed. Because of the rigid compressive association of the crystal 106 rear face and the bias carrying leads or wires 146, there is no relative movement between positive potential and ground. Accordingly, no electrical noise generated by varying capacitance is developed. Similarly, because the leads 144 within the channel 118 of stem 116 are rigidly retained, no electrical noise may be generated due to capacitance variation along that extent of the lead wire. The only unsupported component of lead 144 is at the location where it exits from the rear of stem 116 at 162 and is essentially immediately attached to the bottom of circuit board 138. Because circuit board 138 is rigidly connected to the rearward portion 124 of crystal mount 120 at slot 136, no relative motion will be imparted to the lead 144 at that small extension. Additionally, it may be noted that the most sensitive (integrator) network components of a preamplification circuit are mounted closely adjacent lead 144 upon circuit board 138. Such components are represented for example generally at 164. The sensitive integrating components also are electrostatically shielded by the grounded thick shoulder portion 62 of detector rearward support 60. As noted above, the component 60 additionally is coupled specifically to system ground.

Looking to the rearward portion of positioning shaft 74, it may be observed that guide boss 78 reappears. Boss 78 performs in conjunction with an orientation boss 166 positioned oppositely therefrom. The bosses 78 and 166 are employed for orienting the forward detector component 50 within the disposable handle component 52 (FIG. 3).

The electrical terminal assembly represented generally at 76 is provided as a subassembly including an electrically insulated polymeric insert 170 which extends within internal shaft cavity 140 from a collar 172 to an internal end 174. The rear face 176 of the terminal assembly 76 supports five electrical contacts, thee of which are seen at 178. These five discrete electrical contacts or surfaces 178 are arranged in a predetermined pattern so as to cooperate with the contacts of the electrical contact and sealing assembly 102 (FIG. 3). Preferably, the contacts are spaced radially at 720 intervals and will carry the electrical functions of ground, positive bias, circuit power, a contact carrying the signal from the detector 106 and associated preamplifier and a common contact. Insert 170 is adhesively attached to positioning shaft 74 utilizing an epoxy adhesive.

Figure 5:
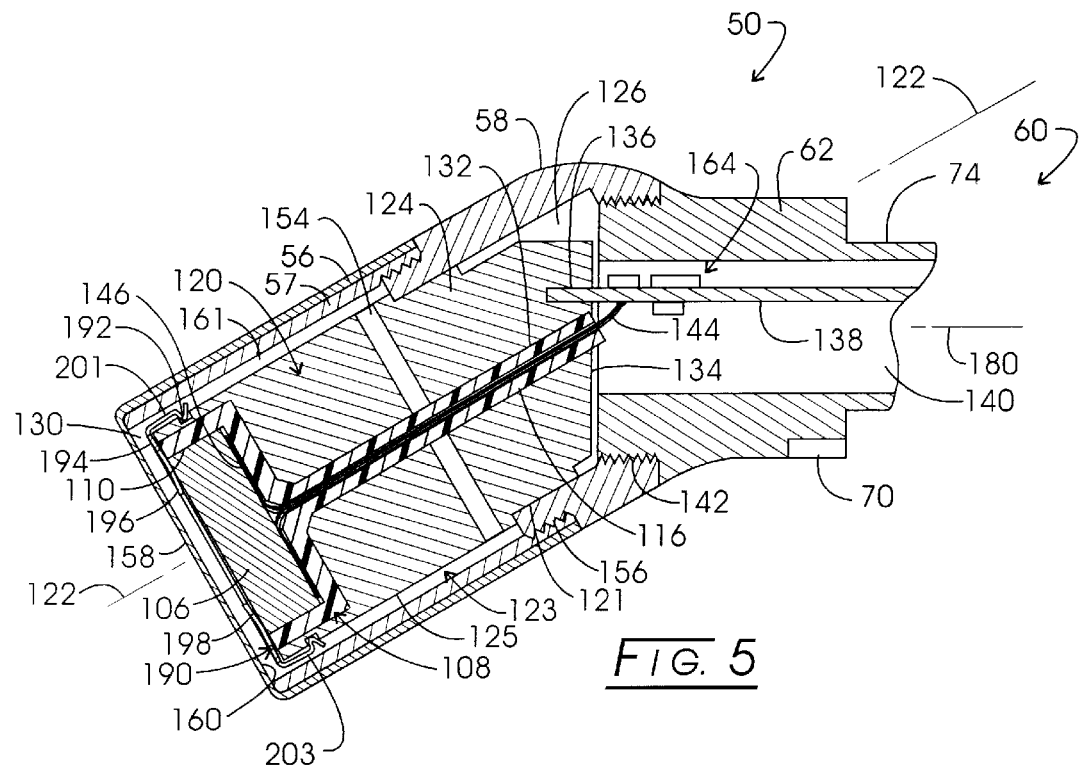
FIG. 5 is a partial sectional view of a detector component according to the invention.
Figure 6:
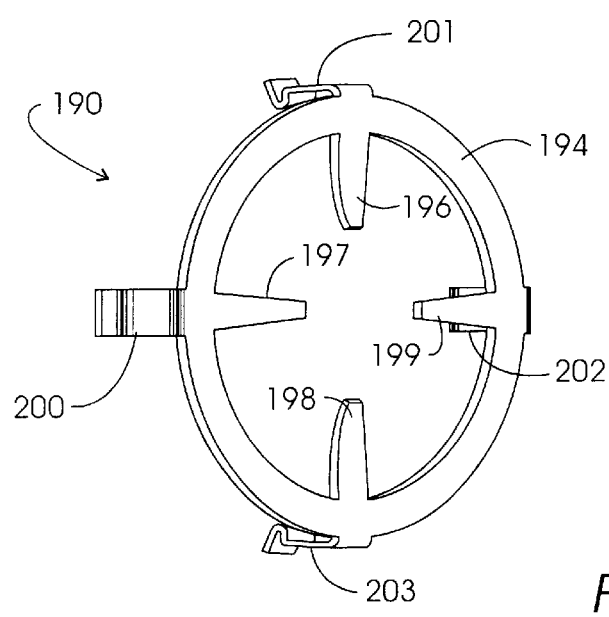
FIG. 6 is a perspective view of a retainer and grounding assembly employed with the embodiment of FIG. 5.

Referring to FIGS. 5 and 6, the forward detector component 50 again is illustrated. In FIG. 5, the structuring of component 50 is seen to be substantially similar to that shown in FIG. 4 with the exception that a preferred retainer and grounding assembly is provided as represented generally at 190. To facilitate the description, the components having commonality with FIG. 4 are identified with the same numeration. In FIG. 5, the earlier described annular groove 152 for retaining o-ring 150 is replaced with a smaller and more forwardly positioned retainer groove 192. FIG. 6 reveals that the retainer and grounding assembly 190 is formed as a flat annular ring 194, the inward surface of which is positioned upon and is coextensive with the crystal mount forward cavity edge 130. Formed of a resilient metal such as a beryllium-copper alloy which may be coated with a metal such as gold, the assembly 190 further includes four integrally formed and inwardly depending resilient ground conveying tines 196–199. Also integrally formed with the ring 194 are symmetrically disposed dogs, four of which are seen at 200–203. The term "dogs," as used herein, is intended to mean any resiliently engaging retainer. Dogs 200–203 resiliently snap into engagement with the retainer groove as seen in FIG. 5 in connection with dogs 201 and 203. Because the resilient tines 196–199 are normally inwardly bent, they will impose a compressive stress upon the forward face of detector crystal 106. In this regard, tines 196 and 198 are seen carrying out that function in FIG. 5. Because the forward face of detector crystal 106 may be coated with a very thin layer of gold, the resulting gold on gold contact with assembly 190 reduces triboelectric noise phenomena caused by the contact of dissimilar materials. Because of their diminutive size, the tines 196–199 do not excessively block impinging radiation. They also function to convey ground from the connection of the assembly 190 with crystal mount 120. Inasmuch as the retainer and grounding assembly 190 is formed of resilient metal, the resultant forward detector component 50 may be heat sterilized, for example by autoclaving.

Figure 7:
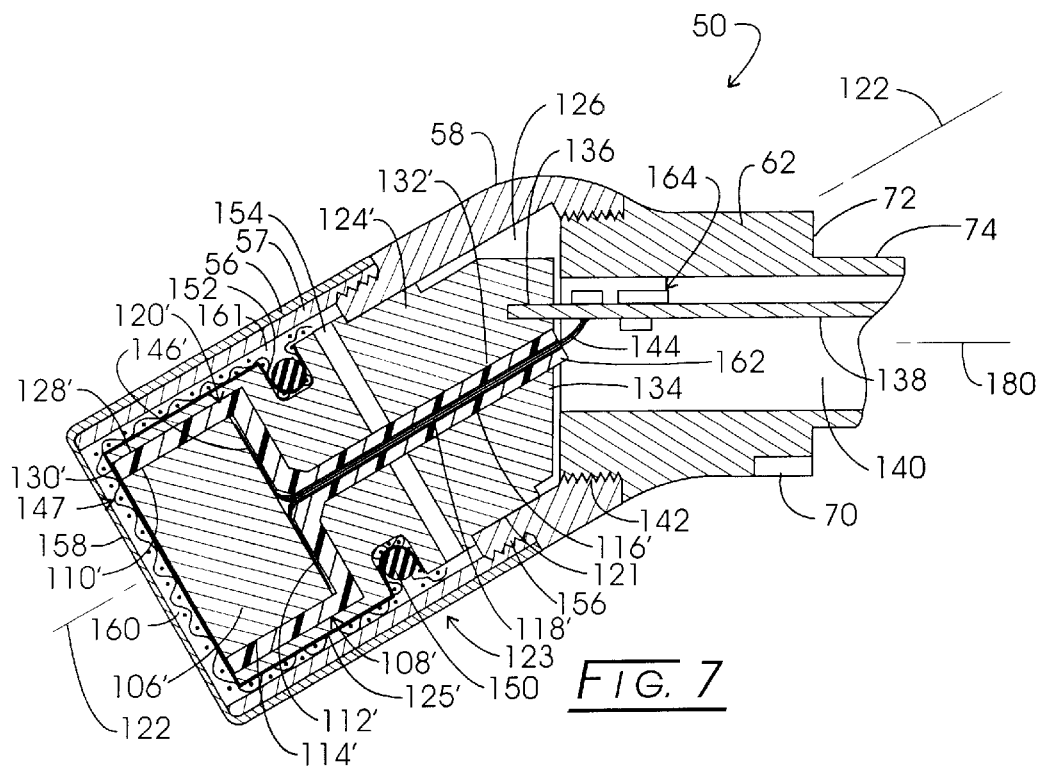
FIG. 7 is a partial sectional view of a forward detector component according to the invention and showing its implementation with a thicker detector crystal.

Referring to FIG. 7, a modification of the probe structure of FIG. 4 to accommodate the thicker crystal for the total trapping mode of operation is revealed. In the figure, those components of the forward detector component 50 which are unchanged are identified with the same numeration provided in conjunction with FIG. 4. Those components which have been altered are shown with the same numeration but in primed fashion. In the latter regard, an advantageous structuring of the component 50 remains wherein the detector crystal 106' is rigidly mounted and all bias carrying electronics are rigidly mounted to avoid noise due to varying capacitance phenomena. As before, no adhesives or cushioning structures are employed in mounting the crystal detector. FIG. 7 reveals that the cadmium-telluride crystal 106' is twice the thickness as that described at 106 in FIG. 4. To accommodate for this greater thickness, the crystal receiving cavity 110' of crystal receiver 108' is enlarged to have twice the depth described earlier. As before, the interior sidewall surfaces 114' of the receiver 108' are in close abutting adjacency with the sides of crystal 106'. Additionally, bottom surface 112' of the receiver 108' supports the splayed leads 146 of the lead grouping 144. The bottom surface of the crystal 106' compressibly retains these leads in position without the intervention of adhesives or the like. The receiver 108' is formed having an integrally fashioned stem 116' with an internal channel 118'. This assures that there is no relative movement between the stem and the forward cavity defining components and thus, no movement of the bias carrying leads 144. To retain the crystal 106' in place, as before, a nylon web 148 is stretched over the forward face of crystal 106' as well as forward cavity edge 130' of the crystal mount 120'. The nylon web 148, as before, is secured by a polymeric o-ring 150 which is retained in an annular groove 152. Additionally as before, the crystal retainer 108' may be formed of polytetrafluoroethylene.

Figure 8:
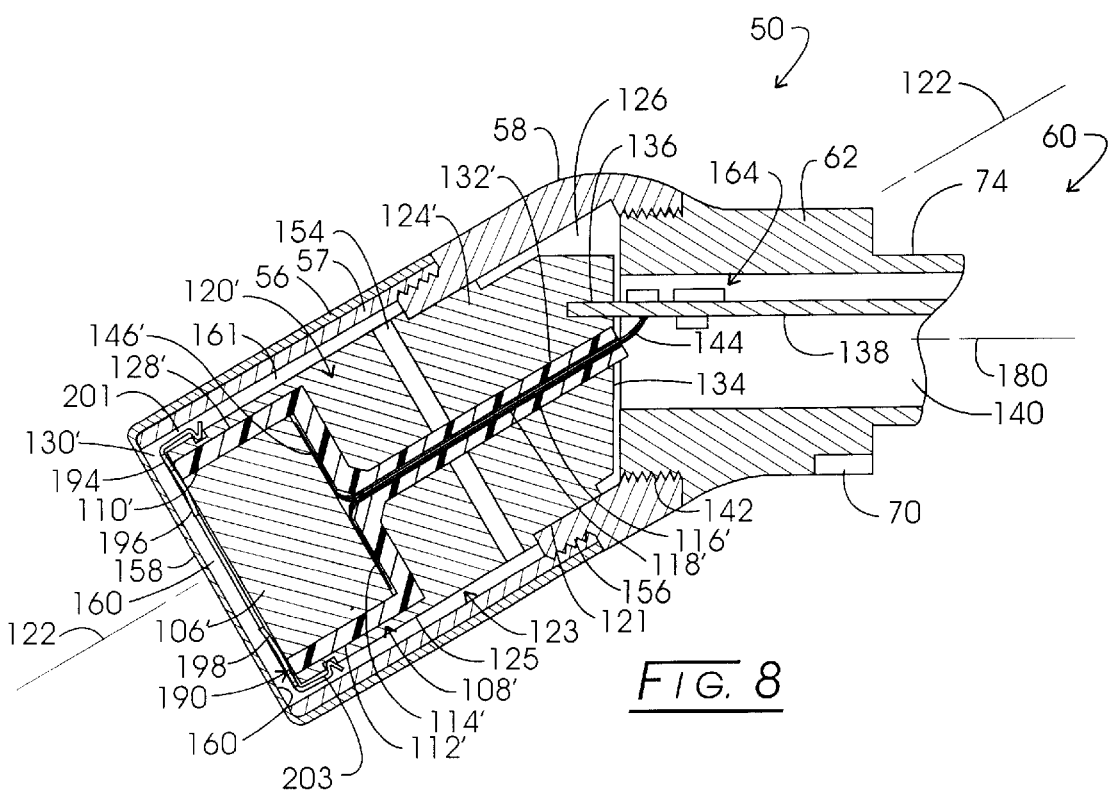
FIG. 8 is a partial sectional view of a forward detector component according to the invention showing its instrumentation with a thicker detector crystal.

Referring to FIG. 8, the forward detector component 50 is illustrated in combination with the noted thicker crystal detector 106' and the retainer and grounding assembly 190 described in connection with FIGS. 5 and 6 in association with the thinner crystal embodiment. Those components which vary from FIGS. 5 and 6 are shown in primed fashion but with the same numerical identification. In this regard, the crystal receiver 108' is configured of an electrically insulative polymeric material having a crystal receiving cavity 110' of increased depth extending to a bottom surface 112'. The interior sidewall surface 114' of the cavity 110' is seen to be in supporting, abutting relationship with the sides of crystal detector 106'. The stem of the receiver 108' at 116' is formed integrally therewith for achieving structural rigidity and contains, as before, a channel 118' for carrying the leads 144. The rearward face of crystal 106' is retained in compression against the splayed array of wire leads 146 which extends from the lead 144. Additionally as before, ground is asserted, as well as compressive stress, at the forward surface of detector crystal 106' by inwardly depending resilient ground conveying tines 196–199 (FIG. 6). The same material selections are made for the embodiment of FIG. 8 as in the earlier figures.

Figure 9:
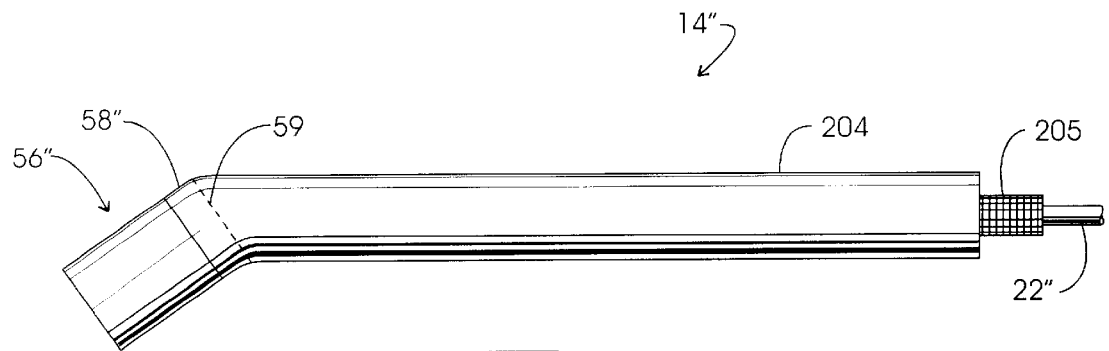
FIG. 9 is a side view of another embodiment of the probe apparatus of the invention.
Figure 10:
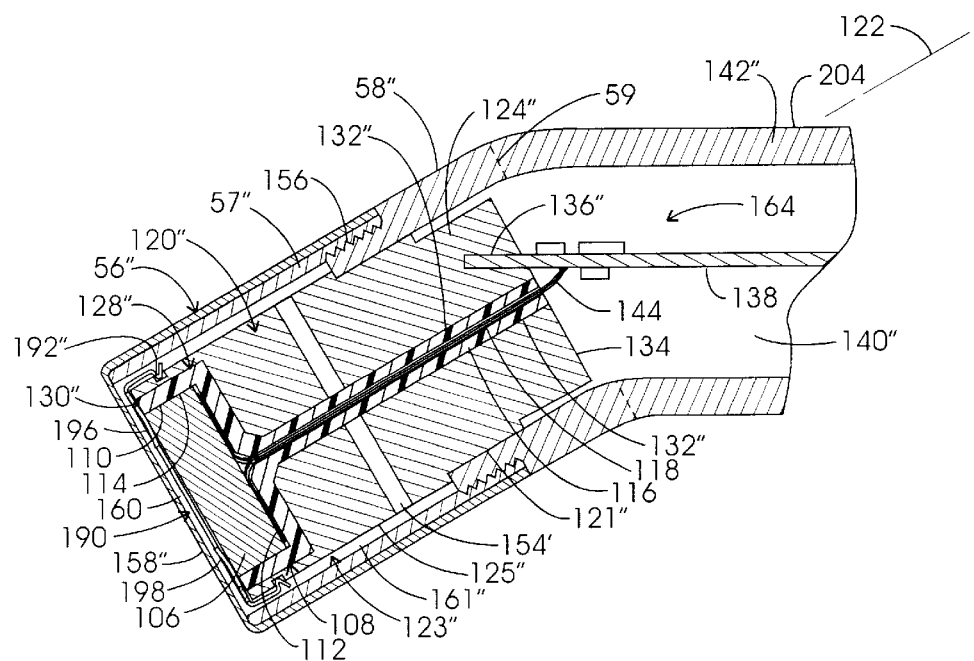
FIG. 10 is a partial sectional view of the probe apparatus of FIG. 9.

A unitary embodiment of the probe apparatus of the invention is depicted in FIGS. 9 and 10. The basic detector components as described above remain with this embodiment, however, a variation occurs in the shape of detector forward support 58 and crystal mount 120. Accordingly, where components of the probe remain unchanged from the earlier embodiment, they are identified with the same numeration as earlier employed. Where the above-noted changes are made to the components, then that same numeration is repeated in double primed fashion.

Referring to FIG. 9, the probe 14" is shown incorporating revised detector forward support 58" and cup-shaped window assembly 56". These components are coupled with a cylindrical handle 204, while the cable 22" of transmission assembly 20 is connected to the handle 204 via a removable connector 205.

Looking to FIG. 10, detector forward support "58" is coupled to handle 204 at an angle of, for example, 15 degrees then rotated 180 degrees before being welded into a single assemblage as shown at dashed line 59. The forward support at 58" and handle 204 combine to provide an internally disposed cavity shown at 140" within which circuit board 138 is disposed. The rearward portion 124" of mount 120" is attached, utilizing an electrically conductive epoxy adhesive, to the forward portion of detector forward support 58" as at 121". As before, this provides a relatively massive cantilevered form of mounting structure for ultimately supporting the crystal detector 106. Crystal mount 120", being formed of material attenuating radiation such as lead, brass or the like, extends forwardly from its connection at 121" to provide a cylindrical surface 125" extending to a mount cavity edge 130" of a mount cavity 128". As before, a centrally disposed access channel 132" extends from the bottom surface of cavity 128" to the rear surface 134". Within the mount cavity 128" there is positioned a crystal receiver 108 with a crystal receiving cavity 110, bottom surface 112 and interior sidewall surface 114. Integrally formed stem 116 extends in tight securement within the channel 132" to the mount rear surface 134". A multi-strand electrical lead 144 extends through the stem 116 and the strands thereof are spread apart in splayed or spider-like fashion at the bottom surface 112. A detector crystal 106, such as cadmium-telluride is mounted within the cavity 110 and is retained in position by a retainer and grounding assembly 190. This latter assembly is the preferred one described in connection with FIGS. 5 and 6 above.

Cup-shaped window assembly 56" is again seen to be formed having a cylindrical, interiorally disposed side shield "57" formed of material attenuating radiation such as tungsten. Shield "57" is threadably engaged with the forward portion of forward support 58" at a cylindrical threaded connector region 156. Side shield "57" buttresses and supports the aluminum component of the window assembly 56" including the thinner forward face 158 to define the earlier noted forward gap 160, as well at the thicker side components. The isolating side gap 161" remains to physically isolate the forward portion of the mount 120" from slight impacts which may be occasioned in the use of the probe assembly 141". As before, a grove 192" functions to receive the spring biased, integrally formed dogs 200–203 of the retainer assembly 190 (FIG. 6). As is apparent, the probe 14" employs a cadmium-telluride crystal of 2 mm thickness intended for utilization in the RIGS surgical procedure in conjunction with lower gamma energy level radionuclides.

Figure 11:
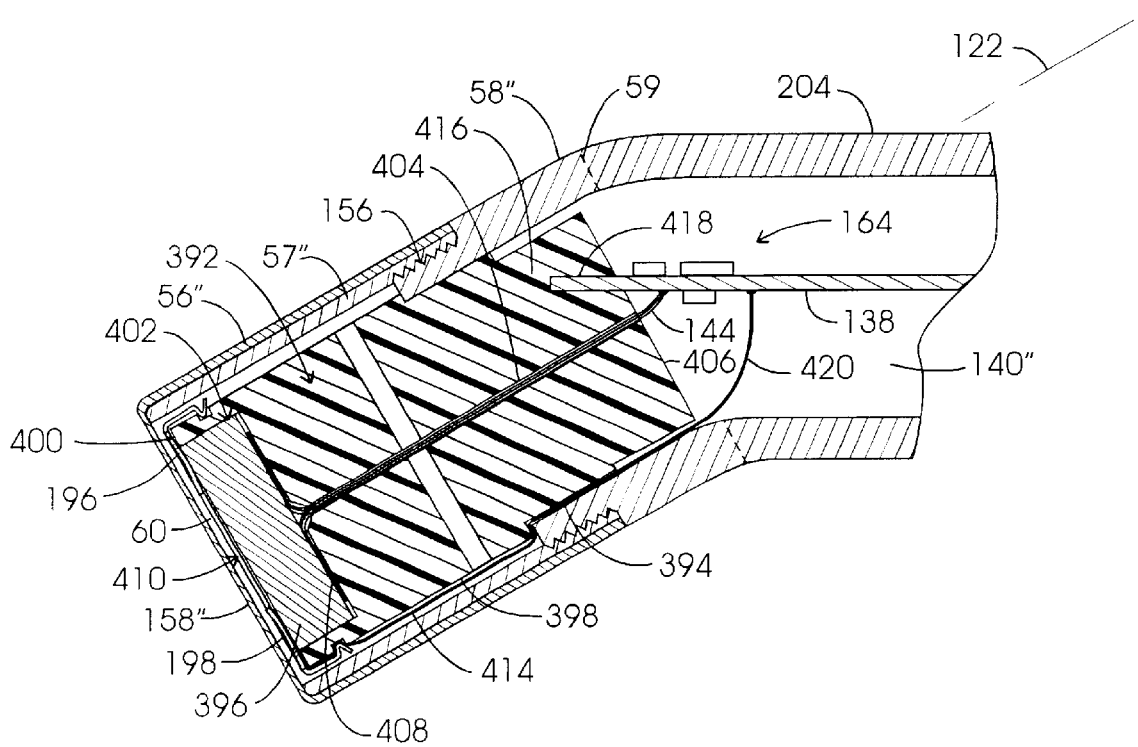
FIG. 11 is a partial sectional view another forward structure for the probe apparatus of FIG. 9 showing its instrumentation with a polymeric crystal mount.

Referring to FIG. 11, a modification of the probe structure of FIG. 10 to accommodate a polymeric crystal mount 392 is revealed. In the figure, those components of the probe which remain unchanged from FIG. 10 retain their prior numeration. FIG. 11 includes cup-shaped window assembly 56" having a cylindrical, interiorally disposed side shield "57". Because side shield "57" is formed of material attenuating radiation, such as tungsten, crystal mount 392 may be formed of material which does not attenuate radiation or electrically insulative, polymeric material. In the present embodiment, the rearward portion of crystal mount 392, formed of a polymeric material, is attached utilizing an epoxy adhesive, to the forward portion of detector forward support 58" as at 394 to provide a cantilevered form of mounting structure for supporting the crystal detector 396. Crystal mount 392 extends forwardly from its connection at 394 to provide a cylindrical surface 398 extending to a mount cavity edge 400 of a mount cavity 402. A centrally disposed access channel 404, of smaller diameter than that shown in FIG. 10, extends from the bottom surface of cavity 402 to the rear surface 406 of mount 392. Because crystal mount 392 is formed of polymeric material, the crystal receiver and integrally formed stem shown in FIG. 10 are not present in FIG. 11. A multi-strand electrical lead assembly extends through and is retained within access channel 404 and the strands thereof are spread apart in splayed or spider-like fashion at the bottom surface 408. A crystal detector 396, such as cadmium-telluride, is mounted within the cavity 402 and is retained in position by a retainer assembly 410. Crystal detector 396 is dimensioned in thickness, being 2 mm, for the purpose of carrying out the RIGS procedure. Without the crystal receiver described in connection with FIG. 10, a crystal detector 396 may be provided with greater diameter and, thus, surface area which is beneficial given the relatively low quantity and energy level radionuclide associated with the RIGS procedure. As before, a groove 412 functions to receive the spring biased, integrally formed dogs 200–203 of the retainer assembly 410 (FIG. 6). Forward gap 160 is defined by the forward looking portion "158" of window assembly 56" as previously described, acting as an acoustic filter, while isolating side gap 414 remains to physically isolate the forward portion of the mount 392 from slight impacts which may be occasioned in the use of probe assembly "14".

In order to prevent the development of varying capacitance induced noise, described earlier in connection with FIG. 4, the radiation attenuating crystal mount must be specifically grounded. However, where the crystal mount is formed of electrically insulative, polymeric material, as in FIG. 11, such specific grounding of the crystal mount 392 is not present. Grounding of the forward surface of crystal detector 396 is provided by a ground wire 420 which extends from circuit board 138 to the metal retainer 410. Inclusion of a polymeric crystal mount 392 avoids varying capacitance induced noise in as much as a substantial distance exists between the biased leads at surface 408 and grounded structure.

Rigid mounting of the interior components within probe 14" continues to prevent the development of other capacitance induced noise as is also described in connection with FIG. 4. Because of the rigid, compressive association of the crystal 396 rear face and the bias or lead carrying wires 144, there is no relative movement between positive potential and very distant ground. Accordingly, no electrical noise as may be generated by varying capacitance is developed. Similarly, because the leads 144 within access channel 404 are rigidly retained and quite distant from a grounded surface, there is no varying capacitance induced noise created. The only unsupported component of lead 144 is at the location where it exits from the rear of access channel 404 and is essentially immediately attached to the bottom of circuit board 138, but because circuit board 138 is rigidly connected to the rearward portion 416 of crystal mount 392 at slot 418, no relative motion will be imparted to the lead 144 at that small extension.

Figure 12A:
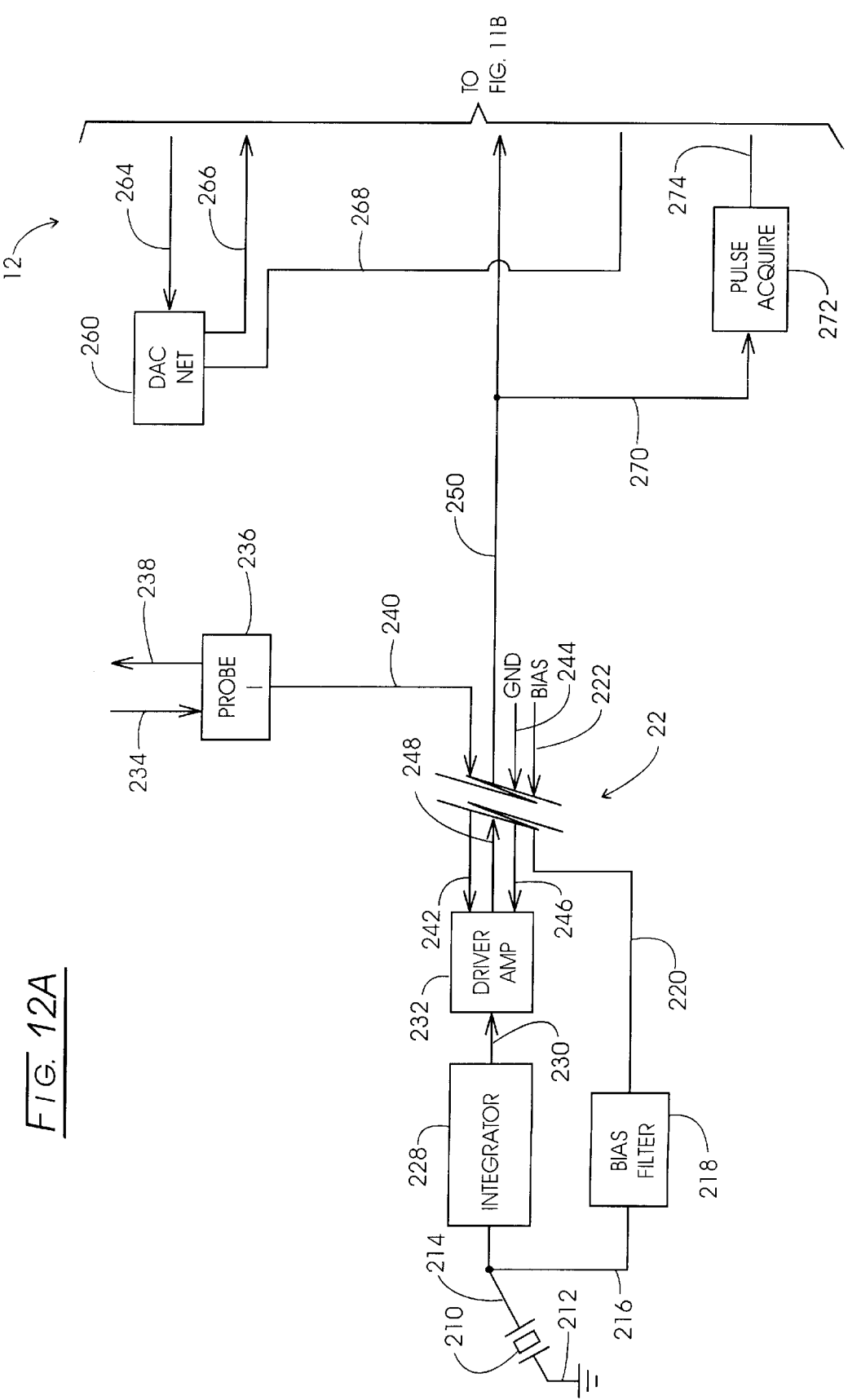
FIGS. 12A and 12B combine as labeled thereon to provide a block diagrammatic representation of the circuit employed with the control assembly and the probe shown in FIG. 1.
Figure 12B:
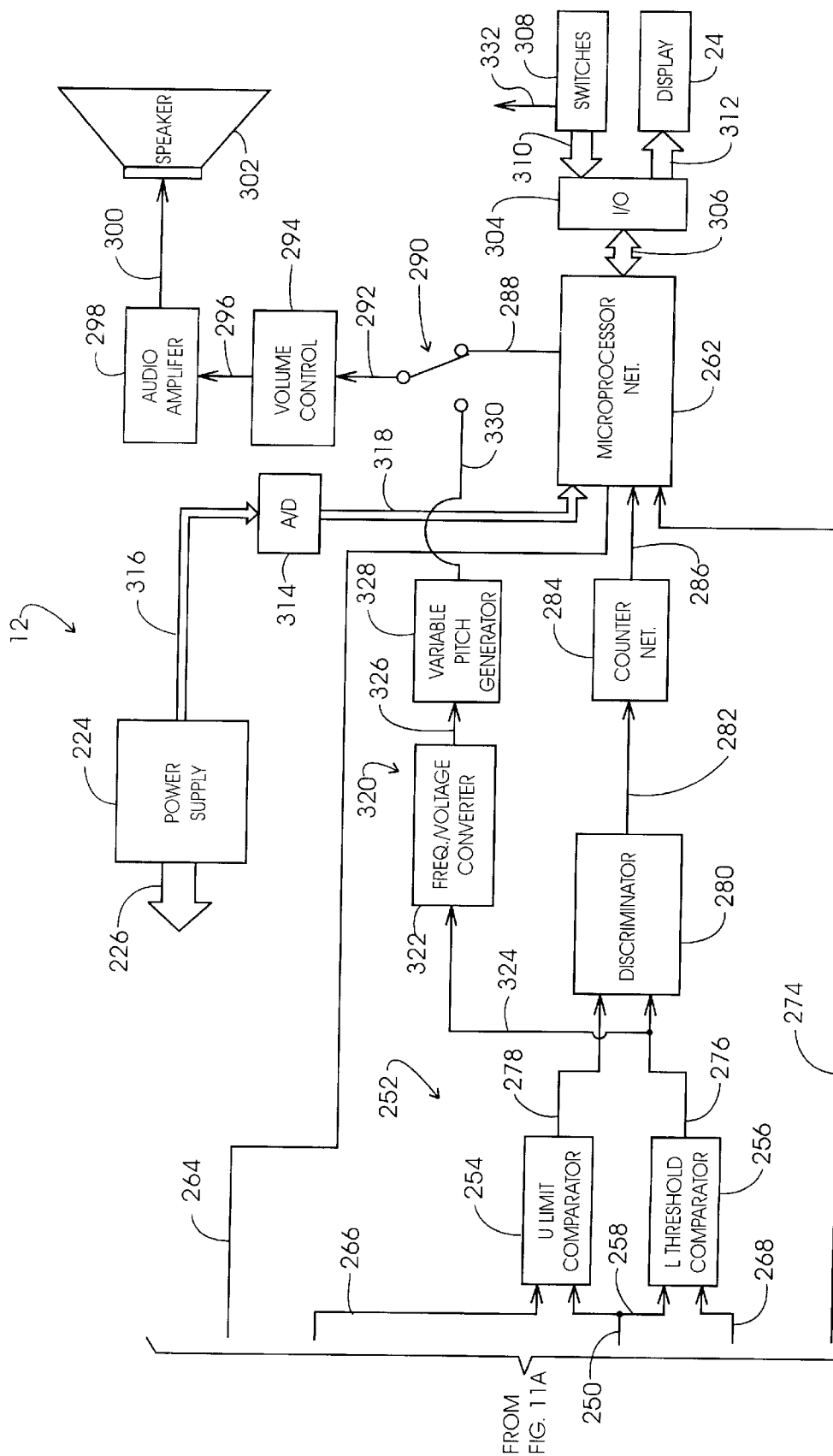

Referring to FIGS. 12A and 12B, a block diagrammatic representation of the circuitry employed with the system 10 is portrayed. These figures should be considered in mutual adjacency in the manner labeled thereon. In FIG. 12A a crystal such as a cadmium-telluride crystal suited for mounting within the detector forward portion 50 is represented at 210. Crystal detector 210 is shown having one face coupled to ground through line 212, while the opposite, biased face thereof is coupled via lines 214 and 216 to a bias filter represented at block 218. The input to filter 218 is represented at line 220 as being applied through the cable as described earlier at 22, which number reappears in the instant figure. The bias input, as represented at line 222, emanates from a multi-output power supply shown in FIG. 12B at block 224. These various outputs are represented, in general, by an arrow 226 extending from block 224.

Returning to FIG. 12A, line 214 from crystal detector 210, carrying a detector output corresponding with radiation emissions impinging upon the detector, is seen to extend to an integrator stage represented at block 228. The integrator stage 228 has been discussed in connection with components 164 in FIG. 5. In this regard, they are mounted in a highly rigidified mechanical structure and within a grounded shield shoulder component 62. As noted earlier, the integrator stage 228 forms part of the preamplification function mounted upon circuit board 138. The integrated valuation of detected radiation emissions then is shown directed, as represented by line 230 to a driver amplification network shown at block 232. A preferred preamplification circuit comprised of blocks 228 and 232 is described in U.S. Pat. No. 5,441,050 by Thurston and Olson, issued Aug. 15, 1995 entitled "Radiation Responsive Surgical Instrument," assigned in common herewith and incorporated herein by reference. A d.c. power supply is provided from the power supply represented at block 224 and arrow 226 (FIG. 12B) for the preamplification function. This power supply is directed, as represented at line 234, to a probe current network represented at block 236. Under microcomputer control, as represented at line 238, the network 236 develops signals, for example, determining whether the probe instrument 14 has been properly connected to the console 12. Delivery of the d.c. power supply for the preamplification function is represented at lines 240 and 242. Line 242 forms a component of flexible cable 22. Electrical ground is generated from the power supply described at block 224 and arrow 226 in FIG. 12B and is shown to be extended by a line 244 within the control assembly 12, as well as line 246 within the probe 14. The preamplifier is a portion of the treatment circuit located within the internal shaft cavity 140 which applies ground and bias to the crystal detector 210. Such regard, ground is provided to the detector forward support housing 58, the crystal mount 120, the window assembly 56 and the detector rearward support 60. The preamplifier electrically treats the detector output of the detector crystal 210 to provide output signals corresponding therewith along line 248 of cable 22 for introduction to the control assembly 12, the corresponding signal carrying line of which is shown at line 250. Line 250 extends to the input of an energy window network represented in FIG. 12B in general at 252. Network 252 functions to evaluate the count output to derive validated photon count signal. Looking to FIG. 12B it may be observed that the energy window network 252 includes an upper limit comparator represented at block 254, as well as a lower threshold comparator represented at block 256. The count output or photon event signals at line 250 are submitted simultaneously to each of these comparator functions 254 and 256, as represented at line 258. Correspondingly, the comparison values or limits associated with the upper limit comparator 254 are applied from a digital-to-analog converter (DAC) seen in FIG. 12A at block 260. Converter 260 is under the control of a microprocessor network represented at block 262 (FIG. 12B), such digital control to device 260 being asserted at line 264. The upper limit value asserted at the comparator 254 is provided at line 266 from DAC 260. Correspondingly, the lower threshold value for comparator function 256 is asserted from DAC 260 via line 268. FIG. 12A also reveals that the signals at line 250 are directed, as represented at line 270, to a pulse acquire function represented at block 272. Network 272 functions, when activated by the microprocessor network 262, to acquire the value of the highest pulse amplitude witnessed at line 250. Periodically, this information then is transmitted to the microprocessor network 262 as represented by line 274. Representing a form of peak detector, the network 272 sometimes is referred to as a "snapshot circuit." With the arrangement shown, the probe 14 assemblage derives count outputs in response to photon emissions which are confronted at the forward face of crystal detector 106 and shown at 210 in FIG. 12A. Those count outputs will have an amplitude corresponding to the energy of interest of the photon emissions. Additionally, the signals may represent spurious phenomena such as cosmic rays, Compton scattering, capacitance variance noise, piezoelectric effects and the like. Accordingly, the energies of the count outputs or amplitudes thereof are evaluated at the energy window network 252 as seen in FIG. 12B. In order for the network 252 to work effectively, it is important to have the signals representing energy of interest well spaced in terms of energy from the noted noise phenomena. Effective windowing has been found to be associated with the mode of operation of the compound crystal detector. That performance mode is selected with respect to the radionuclide energies involved.

Lower threshold comparator function 256 will promulgate a pulse at line at 276 when the signal asserted thereat exhibits an amplitude of value equal to or above a threshold value established, as noted above, from line 268. Correspondingly, the count output signals from line 250 will be evaluated by the upper limit comparator function 254 such that when the count output signal exhibits an amplitude of value above the upper limit value established from line 266, a pulse will be promulgated at line 278. For the RIGS component of the system 10, the outputs from lines 276 and 278 then are directed to the input of an asynchronous, sequential, fundamental mode discriminator circuit represented at block 280. Circuits as at block 280, while being sequential in nature, are not synchronized in any way with a clock signal. Such circuits as at block 280 are described in U.S. Pat. No. 5,475,219 by Olson, entitled "Validation Of Photon Emission-Based Signals Using An Energy Window Network In Conjunction With A Fundamental Mode Discriminator Circuit," issued Dec. 12, 1995 and assigned in common herewith. The discriminator function represented at block 280 serves to generate photon event outputs for count associated signals in the form of finite pulses at line 282. Such pulses occur with the presence of a count output signal at line 250 which represents a photon emission which is valid from the standpoint of the energy range of interest associated with it.

The pulsed signals at line 282 are provided to a counter network represented at block 284. These pulses at line 282 are counted by the network 284, whereupon, as represented at line 286, count data is submitted to the microprocessor network 262 for statistical analysis. The function of counter network 284 maybe implemented in software as described in the above-referenced U.S. Pat. No. 4,889,991. Microprocessor network 262 performs under a variety of operational modes depending upon the user inputs to the function switches at array 28 (FIG. 1) as well as any calibration activity undertaken by the user. In general, it functions to provide outputs to two output components, one aural type generated from a speaker, and the other a visual output at display 44. Generally, a "siren" type of signal manifested with a predetermined frequency variation is asserted as represented by line 288 through a mode switch 290 and line 292 to a volume control function represented at block 294. A volume adjustment having been carried out at the control 294, the volume adjusted signal is directed, as represented at line 296 to an audio amplification circuit represented at block 298. The circuit at block 298, in turn, as represented at line 300, drives a speaker 302. With the noted "siren" arrangement, the frequency output from speaker 302 increases with an exponential change from 20 Hz to 1200 Hz when the average count rate determined by system 10 exceeds a preset threshold level which is statistically significant over background count rates. The "siren" mode is accessed by the user from console 12 by sequentially actuating switch 36 then switch 34. This "siren" mode of performance is described in detail in the above-referenced U.S. Pat. No. 4,889,991 by Ramsey and Thurston.

Microprocessor network 262 performs in conventional fashion with an input/output network as represented at block 304 and dual directional arrow 306. This input/output port function 304 provides for appropriate scanning of pertinent console 12 mounted switches, as represented at block 308 and arrow 310. The output port also drives the display 24, again represented by the same numeration in block form as represented by arrow 312. Further, the microprocessor network 262 may be employed to monitor the performance of the power supply represented at block 224. This is shown being carried out by the interaction of microprocessor network 262 with an analog-to-digital converter represented at block 314 and having an association represented by arrows 316 and 318. The converter 314 functions to digitize analog values at the power supply 224 for submittal to microprocessor network 262.

Components of the adjunct circuitry of system 10 are represented in general at 320 in FIG. 12B. This adjunct system performs in conjunction with higher energy level radionuclides such as $^{99m}$Tc and with probe structures which are configured and operated in a trapping-dependent mode. The components of system 320 include a frequency-to-voltage converter represented at block 322 which responds to the count associated signals from the lower threshold comparator at block 256 as represented at lines 276 and 324 to provide a rate output level signal at line 326 corresponding with the frequency of those count associated signals. This signal will be provided as a d.c. voltage level which extends within a dynamic range of, for example, 0 to 2.5 volts. That signal then is directed to a variable pitch generator function represented at block 328. The generator at block 328 serves to provide the noted initial ranging feature and a count rate thresholding feature which may be controlled from knob 48 or the up/down switches 40 and 42 (FIG. 1). Additionally included in the function 328 is a post-thresholding amplification network having a gain corresponding with the threshold level value to permit full scale performance of the speaker 302 and linear LED array 44 (FIG. 1). The output of the generator function 328 is shown at line 330 extending to one terminal of switch 290. Microprocessor network 262 continues to provide volume control during the operation of generator function 328 in response to the actuation of switch 38 (FIG. 1). An output represented at arrow 332 extends to a "beep" generator function which provides an axillary audible switch feedback for the user.

Referring to FIG. 13, a block diagrammatic representation of the generator function 328 is provided. The figure reveals that the output from the converter network 322 at line 326 is directed to a range select function represented at block 340. Function 340 provides for the earlier-described selection of ranges of counts per second such that an initial approach is taken to derive full-scale drives for the visual and oral cueing components, i.e., LED array 44 and speaker 302. Upon selecting an appropriate range, the range adjusted signal level is directed, as represented at line 342 to block 344 whereat a threshold is established with respect to the incoming signal at line 342. That threshold represents a percentage of full scale or full dynamic range of the signal. Additionally, minimum and maximum values to which a threshold percentage can be set are developed. Without more, where high thresholds are employed, the signal level available for developing a drive for the LED array 44 or speaker 302 would be inadequate. A minimum threshold level may be imposed to avoid sound outputs resulting from environmental noise. Such noise essentially is always at hand, being found to be stronger in some geographic areas than others. The adjusted count rate signal at line 346 is directed to a post threshold amplification network represented at block 348. Network 348 is configured having a gain which corresponds with the threshold level value set at function 344 such that it carries out an amplification of the adjusted count rate signal at line 346 to provide an amplified count rate signal at line 350. That amplified signal lies at levels within a predetermined output dynamic range. The dynamic range is established by the aural cueing and drive demands of the LED array or bar graph 44. In this regard, line 350 is tapped at line 352 and the signal thereat is directed to a bar graph driver function represented at block 354. Driver 354 then drives the array 44 as represented at line 356. Line 350 also is seen directed to a variable pitch generator represented at block 358 which functions to produce a drive signal at line 360 which is directed to line 330. The signal line 330 will then produce a speaker drive output at a pitch corresponding with the drive signal asserted thereat and which lies between a 0 pitch level and a maximum pitch level which corresponds with the noted dynamic range that is maintained. Because, for the present embodiment, the microprocessor driven aural feedback from operation of the switches 308 is not present, an additional "beep" generator is provided as represented at block 362. Generator 362 functions to generate a "beep" via line 360 and 330 at such time as any one of the switches 308 are actuated by the operator. Line 330 is reproduced from FIG. 12B as well as the designation for switch 290, line 288, and line 292.

Referring to FIG. 14, a simulated multi-channel analyzer (MCA) plot is depicted showing two modes of crystal detector operation or performance which are utilized in conjunction with system 10. Where the cadmium-telluride crystal detectors are used for the RIGS procedure, with relatively thin (2 mm) CdZnTe crystals, as discussed above in connection with FIGS. 4 and 5, excellent performance of the detectors is achieved. For the RIGS procedure, a low gamma energy radionuclide, $^{125}$I is used (27 to 35.2 Kev). Accordingly, as a gamma ray contacts the forward face of the crystal detector, holes are captured immediately at the grounded or forwardly facing boundary and the electrons (which have a velocity about 12 times that of holes) all travel the same distance within the detector volume. Thus a very high quality or pure and quite expensive crystal structure is not required for the instant implementation and additionally, a high voltage bias is not used. This is a substantial benefit in terms of electronics, cable size, flexibility and the like. As a result, MCA plots such as those represented at plot 370 in FIG. 14 are realized.

The difficulties of operating the cadmium-telluride crystal having a thickness of 2 mm or greater and performing with a relatively higher bias voltage level resides in the location of interactions with an electron within the crystal volume and varying degrees of trapping. This particularly is the case with respect to relatively higher gamma energy sources, for example $^{99m}$Tc. The variation in interaction and variations in trapping result in an MCA plot having a very flat or broad photopeak and a wide energy distribution resulting in poor probe performance for this mode of operation. Plots as at 372 in FIG. 14 may result.

To operate successfully with the relatively higher gamma energy sources, the rigid crystal mounting and circuitry structuring of the invention is modified to the extent that a thicker cadmium-telluride crystal is utilized as discussed above in conjunction with FIGS. 7 and 8, for example the crystal is made having a depth or thickness of 4 mm. Additionally, a relatively lower bias voltage is employed with this thick crystal. This creates a mode of operation which may be deemed a "trapping dependent operational mode." With a relatively low bias and a thicker cadmium-telluride crystal, gamma ray electron interaction will occur throughout the volume of the crystal. However, with this arrangement, the number of electrons reaching the biased side or positive side of the detector crystal approaches zero due to trapping. There now occurs a dominance of trapping time over what would otherwise be the carrier transit time. With this gradual trapping phenomena, even though the electron components of the carriers do not reach the positive face of the detector crystal, they do move and cause a current which is integrated to provide a charge. The charge will be smaller because electrons have been lost and the maximum value of charge will be lowered somewhat. The result in energy and count distribution on an MCA plot will see a desirably sharp curve as at 370, but the curve will move to the left towards a lower energy value as represented at 374. Thus configured, the detector crystal is seen to perform adequately with the higher gamma energy radionuclides. In general, a 60 volt positive bias is employed with the thicker crystals.

Since certain changes may be made to the above described system and apparatus without departing from the scope of the invention herein involved, it is intended that all matter contained in the description thereof and shown in the accompanying drawings shall be interpreted as illustrative and not in a limiting sense.

What is claimed is:

1. Probe apparatus for detecting and locating sources of radiation emission, comprising:

a handle component extending from a rearward end to a forward end, having a handle wall surmounting an interior handle cavity, a detector forward support extending forwardly from said handle component forward end to a forward region with a forwardly facing tip, having a support wall surmounting a support internal cavity and having an externally disposed support connection region at said forward region;

a crystal mount, formed of material attenuating said radiation, having a mount rear portion with a rear surface mounted within said support internal cavity and extending forwardly from said tip with a cylindrical outer mount surface of first diametric extent to a forwardly opening mount cavity with an interior bottom surface and interior side surface extending forwardly to a mount cavity edge, said mount having an access channel extending from said interior bottom surface to said rear surface;

a rigid, polymeric electrically insulative crystal receiver mounted within said mount cavity and having a forwardly opening crystal receiving cavity with an interior bottom surface and an interior sidewall surface extending toward said mount cavity edge;

a bias conveying and signal receiving lead assembly extending from said crystal receiving cavity interior bottom surface through said access channel and into said support internal cavity;

a crystal detector mounted in closely nesting relationship within said crystal receiving cavity, having a rearward face in abutting direct engagement with said lead assembly at said receiving cavity interior bottom surface, said crystal detector extending to a forward face adjacent said mount cavity edge and being responsive to radiation impinging upon said forward face to provide a detector output;

a cup-shaped window assembly including a side portion having an open cylindrical interior surface, having a forward portion of second diametric extent greater than said first diametric extent to define a side gap with said crystal mount, an internally disposed connection region located rearwardly therefrom and said side portion having a side portion length extending between a rear edge and a forward end, said forward end extending a forward gap defining distance forwardly from said mount cavity edge when said connection region is connected with said support connection region, and a window, formed of radiation transmissive material extending over said forward end to define said forward gap;

a treatment circuit located within said handle cavity for applying a bias to said crystal detector rearward face through said lead assembly and coupling electrical ground to said crystal mount, and responsive to said detector output to provide output signals corresponding therewith; and a retainer and grounding assembly mounted upon said crystal mount and over said mount cavity edge, abuttably and compressibly retaining said crystal detector against said lead assembly at said receiving cavity bottom surface and abuttably coupling electrical ground from said crystal mount to said crystal detector forward face.

2. The probe apparatus of claim 1 in which said cup-shaped window assembly includes a cylindrical sleeve shield formed of material attenuating said radiation, having an open cylindrical interior surface, said internally disposed connection region being a shield connection region, said sleeve shield extending between a rear edge and a forward edge, said forward edge extending said forward gap distance from said mount cavity edge, and said window extends over said sleeve shield at said forward edge.

3. The probe apparatus of claim 2 in which:

said detector forward support externally disposed support connection region includes an annular shoulder spaced rearwardly from said tip; and said sleeve shield rear edge is in abuttment with said shoulder when said shield connection region is connected with said support connection region.

4. The probe apparatus of claim 3 in which said shield connection region is threadably engagable with said support connection region.

5. Probe apparatus for detecting and locating sources of radiation emission, comprising:

a handle component extending from a rearward end to a forward end, having a handle wall surmounting an interior handle cavity, a detector forward support extending forwardly from said handle component forward end to a forward region with a forwardly facing tip, having a support wall surmounting a support internal cavity and having an externally disposed support connection region at said forward region;

a crystal mount, formed of material attenuating said radiation, having a mount rear portion with a rear surface mounted within said support internal cavity and extending forwardly from said tip with a cylindrical outer mount surface of first diametric extent to a forwardly opening mount cavity with an interior bottom surface and interior side surface extending forwardly to a mount cavity edge, said mount having an access channel extending from said interior bottom surface to said rear surface, said crystal mount being formed having a retainer groove spaced a predetermined distance inwardly from said mount cavity edge;

a rigid, polymeric electrically insulative crystal receiver mounted within said mount cavity and having a forwardly opening crystal receiving cavity with an interior bottom surface and an interior sidewall surface extending toward said mount cavity edge;

a bias conveying and signal receiving lead assembly extending from said crystal receiving cavity interior bottom surface through said access channel and into said support internal cavity;

a crystal detector mounted in closely nesting relationship within said crystal receiving cavity, having a rearward face in abutting direct engagement with said lead assembly at said receiving cavity interior bottom surface, said crystal detector extending to a forward face adjacent said mount cavity edge and being responsive to radiation impinging upon said forward face to provide a detector output;

a cup-shaped window assembly including a side portion having an open cylindrical interior surface, having a forward portion of second diametric extent greater than said first diametric extent to define a side gap with said crystal mount, an internally disposed connection region located rearwardly therefrom and said side portion having a side portion length extending between a rear edge and a forward end, said forward end extending a forward gap defining distance forwardly from said mount cavity edge when said connection region is connected with said support connection region, and a window, formed of radiation transmissive material extending over said forward end to define said forward gap;

a treatment circuit located within said handle cavity for applying a bias to said crystal detector rearward face through said lead assembly and coupling electrical ground to said crystal mount, and responsive to said detector output to provide output signals corresponding therewith; and a retainer and grounding assembly mounted upon said crystal mount and over said mount cavity edge, abuttably and compressibly retaining said crystal detector against said lead assembly at said receiving cavity bottom surface and abuttably coupling electrical ground from said crystal mount to said crystal detector forward face, said retainer and grounding assembly including an electrically conductive annular ring positioned upon said crystal mount at said mount cavity edge, compressibly retained thereon from said retainer groove and including at least one resilient ground conveying tine in compressive abutting engagement with said crystal detector forward face.

6. Probe apparatus for detecting and locating sources of radiation emission, comprising:

a handle component extending from a rearward end to a forward end, having a handle wall surmounting an interior handle cavity, a detector forward support extending forwardly from said handle component forward end to a forward region with a forwardly facing tip, having a support wall surmounting a support internal cavity and having an externally disposed support connection region at said forward region;

a crystal mount, formed of material attenuating said radiation, having a mount rear portion with a rear surface mounted within said support internal cavity and extending forwardly from said tip with a cylindrical outer mount surface of first diametric extent to a forwardly opening mount cavity with an interior bottom surface and interior side surface extending forwardly to a mount cavity edge, said mount having an access channel extending from said interior bottom surface to said rear surface, said crystal mount being formed having a retainer groove spaced a predetermined distance inwardly from said mount cavity edge;

a rigid, polymeric electrically insulative crystal receiver mounted within said mount cavity and having a forwardly opening crystal receiving cavity with an interior bottom surface and an interior sidewall surface extending toward said mount cavity edge;

a bias conveying and signal receiving lead assembly extending from said crystal receiving cavity interior bottom surface through said access channel and into said support internal cavity;

a crystal detector mounted in closely nesting relationship within said crystal receiving cavity, having a rearward face in abutting direct engagement with said lead assembly at said receiving cavity interior bottom surface, said crystal detector extending to a forward face adjacent said mount cavity edge and being responsive to radiation impinging upon said forward face to provide a detector output;

a cup-shaped window assembly including a side portion having an open cylindrical interior surface, having a forward portion of second diametric extent greater than said first diametric extent to define a side gap with said crystal mount, an internally disposed connection region located rearwardly therefrom and said side portion having a side portion length extending between a rear edge and a forward end, said forward end extending a forward gap defining distance forwardly from said mount cavity edge when said connection region is connected with said support connection region, and a window, formed of radiation transmissive material extending over said forward end to define said forward gap;

a treatment circuit located within said handle cavity for applying a bias to said crystal detector rearward face through said lead assembly and coupling electrical ground to said crystal mount, and responsive to said detector output to provide output signals corresponding therewith; and a retainer and grounding assembly mounted upon said crystal mount and over said mount cavity edge, abuttably and compressibly retaining said crystal detector against said lead assembly at said receiving cavity bottom surface and abuttably coupling electrical ground from said crystal mount to said crystal detector forward face, said retainer and grounding assembly including a flat ring formed of resilient metal positioned upon and coextensive with said mount cavity edge and compressibly retained thereon from said retainer groove, said ring including a plurality of inwardly depending ground conveying tines in compressive abutting engagement with said crystal detector forward face.

7. The probe apparatus of claim 6 in which said annular ring includes at least two resilient integrally formed dogs depending therefrom and in engagement with said retainer groove for compressibly retaining said annular ring upon said crystal mount and conveying said ground.

8. The probe apparatus of claim 7 in which:
   said forward face of said crystal detector is configured with a surface coating of a given metal; and
   said retainer and grounding assembly is configured with a surface coating of said given metal.

9. Probe apparatus for detecting and locating sources of radiation emission, comprising:
   a handle component extending from a rearward end to a forward end, having a handle wall surmounting an interior handle cavity,
   a detector forward support extending forwardly from said handle component forward end to a forward region with a forwardly facing tip, having a support wall surmounting a support internal cavity and having an externally disposed support connection region at said forward region;
   a crystal mount, formed of material attenuating said radiation, having a mount rear portion with a rear surface mounted within said support internal cavity and extending forwardly from said tip with a cylindrical outer mount surface of first diametric extent to a forwardly opening mount cavity with an interior bottom surface and interior side surface extending forwardly to a mount cavity edge, said mount having an access channel extending from said interior bottom surface to said rear surface;
   a rigid, polymeric electrically insulative crystal receiver mounted within said mount cavity and having a forwardly opening crystal receiving cavity with an interior bottom surface and an interior sidewall surface extending toward said mount cavity edge, said rigid polymeric crystal receiver including an elongate integrally formed stem positioned within and extending through said access channel;
   a bias conveying and signal receiving lead assembly extending from said crystal receiving cavity interior bottom surface through said stem and into said support internal cavity;
   a crystal detector mounted in closely nesting relationship within said crystal receiving cavity, having a rearward face in abutting direct engagement with said lead assembly at said receiving cavity interior bottom surface, said crystal detector extending to a forward face adjacent said mount cavity edge and being responsive to radiation impinging upon said forward face to provide a detector output;
   a cup-shaped window assembly including a side portion having an open cylindrical interior surface, having a forward portion of second diametric extent greater than said first diametric extent to define a side gap with said crystal mount, an internally disposed connection region located rearwardly therefrom and said side portion having a side portion length extending between a rear edge and a forward end, said forward end extending a forward gap defining distance forwardly from said mount cavity edge when said connection region is connected with said support connection region, and a window, formed of radiation transmissive material extending over said forward end to define said forward gap;
   a treatment circuit located within said handle cavity for applying a bias to said crystal detector rearward face through said lead assembly and coupling electrical ground to said crystal mount, and responsive to said detector output to provide output signals corresponding therewith; and
   a retainer and grounding assembly mounted upon said crystal mount and over said mount cavity edge, abuttably and compressibly retaining said crystal detector against said lead assembly at said receiving cavity bottom surface and abuttably coupling electrical ground from said crystal mount to said crystal detector forward face.

10. Probe apparatus for detecting and locating sources of radiation emission, comprising:
   a handle component extending from a rearward end to a forward end, having a handle wall surmounting an interior handle cavity,
   a detector forward support extending forwardly from said handle component forward end to a forward region with a forwardly facing tip, having a support wall surmounting a support internal cavity and having an externally disposed support connection region at said forward region;
   a crystal mount, formed of material attenuating said radiation, having a mount rear portion with a rear surface mounted within said support internal cavity and extending forwardly from said tip with a cylindrical outer mount surface of first diametric extent to a forwardly opening mount cavity with an interior bottom surface and interior side surface extending forwardly to a mount cavity edge, said mount having an access channel extending from said interior bottom surface to said rear surface;
   a rigid, polymeric electrically insulative crystal receiver mounted within said mount cavity and having a forwardly opening crystal receiving cavity with an interior bottom surface and an interior sidewall surface extending toward said mount cavity edge;
   a bias conveying and signal receiving lead assembly extending from said crystal receiving cavity interior bottom surface through said access channel and into said support internal cavity;
   a crystal detector mounted in closely nesting relationship within said crystal receiving cavity, having a rearward face in abutting direct engagement with said lead assembly at said receiving cavity interior bottom surface, said crystal detector extending to a forward face adjacent said mount cavity edge and being responsive to radiation impinging upon said forward face to provide a detector output;
   a cup-shaped window assembly including a side portion having an open cylindrical interior surface, having a forward portion of second diametric extent greater than said first diametric extent to define a side gap with said crystal mount, an internally disposed connection region located rearwardly therefrom and said side portion having a side portion length extending between a rear edge and a forward end, said forward end extending a forward gap defining distance forwardly from said mount cavity edge when said connection region is connected with said support connection region, and a window, formed of radiation transmissive material extending over said forward end to define said forward gap;

a treatment circuit located within said handle cavity for applying a bias to said crystal detector rearward face through said lead assembly and coupling electrical ground to said crystal mount, and responsive to said detector output to provide output signals corresponding therewith, said treatment circuit including an integrator stage having components mounted upon a circuit board, said circuit board being fixed to said crystal mount rear portion, said components being located in close adjacency with said rear portion and said access channel; and a retainer and grounding assembly mounted upon said crystal mount and over said mount cavity edge, abuttably and compressibly retaining said crystal detector against said lead assembly at said receiving cavity bottom surface and abuttably coupling electrical ground from said crystal mount to said crystal detector forward face.

11. The probe apparatus of claim 10 in which said circuit board extends rearwardly outwardly from a rigid mounting with said crystal mount rear portion within said support internal cavity.

12. The probe apparatus of claim 10 in which:

said circuit board extends rearwardly outwardly from a rigid mounting with said crystal mount rear portion at said rear surface;

said circuit board including a circuit surface at said electrical ground; and said circuit surface is electrically coupled with said crystal mount rear surface.

13. A surgical system for detecting and locating sources of radiation emission emanating from tissue of a body, comprising:

a detector assembly, comprising:

a detector forward support having a generally cylindrical outer wall surmounting an interior support cavity and disposed about a detector axis;

a crystal mount formed of metal material attenuating said radiation emission having a generally cylindrical configuration, disposed about said detector axis, having a rearward portion mounted within said support cavity and extending forwardly with a cylindrical outer mount surface, having a forwardly disposed crystal retention cavity opening forwardly along said detector axis, having a cavity interior surface extending to a forward mount cavity edge, and an access channel extending from the bottom of said cavity interior surface through said rearward portion;

a rigid, polymeric electrically insulated crystal receiver mounted within said crystal retention cavity and having a forwardly opening crystal receiving cavity with an interior bottom surface and an interior sidewall surface extending toward said mount cavity edge;

a detector rearward support extending along a support axis, having a shoulder portion fixed to said detector forward support, having a rearwardly depending shoulder surface, and including a positioning shaft extending a predetermined length from said shoulder surface, said shoulder portion and said positioning shaft surmounting an internal shaft cavity communicating with said access channel;

a bias conveying and signal receiving forward lead assembly extending from said crystal receiving cavity bottom surface through said access channel and into said internal shaft cavity;

a cup-shaped window assembly mounted upon said detector forward support over said crystal mount and having a radiation transmissible window portion extending over and spaced from said forward mount cavity edge and said outer mount surface to respectively define a forward gap and a side gap;

a crystal detector mounted in closely nesting relationship within said crystal receiving cavity, having a rearward face in abutting engagement with said forward lead assembly at said receiving cavity bottom surface and extending along a side surface to a forward face adjacent said forward edge, said detector being responsive to radiation passing through said window portion to provide a detector output;

a treatment circuit located within said internal shaft cavity for applying a bias to said detector crystal rearward face through said forward lead assembly, for applying ground to said detector forward support housing, said crystal mount, said window assembly and said detector rearward support and for electrically treating said detector output to provide output signals corresponding therewith;

a retainer and grounding assembly mounted upon said crystal mount and over said forward cavity edge, abuttably, compressibly and rigidly retaining said crystal detector against said forward lead assembly at said receiving cavity bottom surface and abuttibly conveying electrical ground from said crystal mount to said crystal detector forward face; and an electrical terminal assembly mounted upon said positioning shaft and in electrical communication with said treatment circuit;

a disposable handle component, including:

a hand gripable handle housing having a forwardly disposed retainer portion with a receiving cavity configured for removably receiving said positioning shaft to locate it at an operative orientation;

an electrical contact assemblage mounted within said handle housing adjacent said receiving cavity and having electrical contacts mounted thereon engageable in circuit completing relationship with said electrical terminal assembly when said positioning shaft is in said operative orientation;

a flexible electrical transmission cable coupled to said handle housing and having electrical leads connected with electrical contact assemblage electrical contacts and extending to an electrical connector component; and a signal treatment and control assembly having an input connector for removable electrical coupling with said cable electrical connector component and responsive to said output signals conveyed by said cable to provide perceptible output signals.

14. The surgical system of claim 13 in which:

said crystal mount is formed having a retainer groove spaced a predetermined distance inwardly from said mount cavity edge; and said retainer and grounding assembly includes an electrically conductive annular ring positioned upon said crystal mount at said mount cavity edge, compressibly retained thereon from said retainer groove and including at least one resilient ground conveying tine in compressive abutting engagement with said crystal detector forward face.

15. The surgical system of claim 13 in which:

said crystal mount is formed having a retainer groove spaced a predetermined distance inwardly from said mount cavity edge; and said retainer and grounding assembly includes a flat ring formed of resilient metal positioned upon and coextensive with said mount cavity edge and compressibly retained thereon from said retainer groove, said ring including a plurality of inwardly depending ground conveying tines in compressive abutting engagement with said crystal detector forward face.

16. The surgical system of claim 15 in which said annular ring includes at least two resilient integrally formed dogs depending therefrom and in engagement with said retainer groove for compressibly retaining said annular ring upon said crystal mount and conveying said ground.

17. The surgical system of claim 13 in which:
said rigid polymeric crystal receiver includes an elongate integrally formed stem positioned within and extending through said access channel; and
said forward lead assembly extends through and is retained within said stem.

18. A surgical system of claim 13 in which:
said treatment circuit includes an integrator stage having components mounted upon a circuit board; and
said circuit board is fixed to said crystal mount rearward portion, said components being located in close adjacency with said rearward portion and said access channel.

19. The surgical system of claim 18 in which said circuit board extends rearwardly outwardly from a rigid mounting with said crystal mount rearward portion within said internal shaft cavity.

20. The surgical system of claim 13 in which:
said detector forward support, said detector rearward support and said window assembly are formed of metal; and
said detector rearward support is threadably engaged with said detector forward support.

21. The surgical system of claim 13 in which said electrically insulative crystal receiver interior sidewall surface is configured to abuttably engage said side surface of said crystal detector.

22. The surgical system of claim 13 in which:
said electrical terminal assembly includes a predetermined pattern of discrete electrical contacts mounted upon a rearwardly disposed electrically insulative electrical contact support surface;
said electrical contact assemblage within said handle housing includes a predetermined pattern of discrete electrical terminals corresponding with said predetermined pattern of discrete electrical contacts;
a first orienting assemblage positioned upon said positioning shaft; and
a second orienting assemblage positioned upon said handle housing retainer portion and mechanically cooperative with said first orienting assembly to align said discrete electrical contacts in circuit completing relationship with said discrete electrical terminals when said positioning shaft is in said operative orientation.

23. The surgical system of claim 13 in which:
said detector forward support, said detector rearward support and said window assembly are formed of metal;
said detector axis is canted at a predetermined angle with respect to said support axis; and
said detector rearward support is threadably engaged with said detector forward support.

24. The surgical system of claim 13 in which:
said hand gripable handle housing includes a latch assembly having an engagement component spring biased for forward movement;
said detector forward support, said detector rearward support and said window assembly are formed of metal; and
said detector rearward support includes a latching notch extending inwardly in parallel relationship with said support axis from said shoulder surface at a location receiving said engaging component when said positioning shaft is at said operative orientation.

25. The surgical system of claim 24 in which:
said handle housing includes a forwardly disposed contact surface; and
said positioning shaft is locatable at said operative orientation when said shoulder surface is in abutting adjacency with said contact surface.

26. Probe apparatus for detecting and locating sources of radiation emission, comprising:
a hand supportable housing extending from a rearward end to a forward region, having a wall surmounting an interior handle cavity, said wall having a housing connection region;
a crystal mount, formed of electrically insulative material and supported upon said housing forward region and having a forward portion with an outwardly disposed crystal seating surface and a rearward portion with a rear surface, said crystal mount having a cylindrical outer mount surface of first diametric extent;
a bias conveying and signal receiving lead assembly extending from said crystal seating surface into said handle cavity;
a crystal detector having a rearward face supported upon said crystal seating surface in abutting contact with said bias conveying and signal receiving lead assembly and having a side surface extending to a forward face;
a cylindrical sleeve shield formed of material attenuating said radiation, having an open interior surface, surmounting said crystal mount, co-extensive with said crystal detector side surface, and extending to a forward edge;
a window, formed of radiation transmissive material extending over said sleeve shield forward edge;
said sleeve shield and said window being formed as a cup-shaped window assembly, said sleeve shield having an open cylindrical interior surface with a forward portion of second diametric extent greater than said first diametric extent to define a side gap with said crystal mount, an internally disposed sleeve shield connection region located rearwardly from said forward portion and connected with said housing connection region, said sleeve shield having a sleeve shield length extending between a rear edge and a forward end, said forward end extending a forward gap defining distance from said mount cavity edge when said sleeve shield connection region is connected with said housing connection region, and said window extending over said forward end to define said forward gap;
a treatment circuit located within said handle cavity for applying a bias to said crystal detector rearward face through said lead assembly and applying electrical ground to said crystal detector forward face, and responsive to said detector output to provide output signals corresponding therewith; and
a retainer assembly abuttably and compressively retaining said crystal detector against said lead assembly at said crystal seating surface.

27. The probe apparatus of claim 26 in which said crystal mount is formed of rigid, polymeric material.

28. The probe apparatus of claim 26 in which:
said crystal seating surface forms an interior bottom surface of a forwardly opening mount cavity with an interior side surface extending forwardly to a mount cavity edge; and said crystal detector is mounted in closely nesting relationship within said mount cavity, said forward face of said crystal being adjacent said mount cavity edge.

29. The probe apparatus of claim 26 in which said sleeve shield connection region is threadably engaged with said housing connection region.

30. The probe apparatus of claim 26 in which:

said crystal mount has a channel extending from said interior bottom surface into said housing cavity; and said lead assembly extends through and is retained within said channel.

31. Probe apparatus for detecting and locating sources of radiation emission, comprising:

a hand supportable housing extending from a rearward end to a forward region, having a wall surmounting an interior handle cavity, said wall having a housing connection region;

a crystal mount, formed of electrically insulative material and supported upon said housing forward region and having a forward portion with an outwardly disposed crystal seating surface and a rearward portion with a rear surface, said crystal mount having a cylindrical outer mount surface of first diametric extent;

a bias conveying and signal receiving lead assembly extending from said crystal seating surface into said handle cavity;

a crystal detector having a rearward face supported upon said crystal seating surface in abutting contact with said bias conveying and signal receiving lead assembly and having a side surface extending to a forward face;

a cylindrical sleeve shield formed of material attenuating said radiation, having an open interior surface, surmounting said crystal mount, co-extensive with said crystal detector side surface, and extending to a forward edge;

a window, formed of radiation transmissive material extending over said sleeve shield forward edge;

a treatment circuit located within said handle cavity for applying a bias to said crystal detector rearward face through said lead assembly and applying electrical ground to said crystal detector forward face, and responsive to said detector output to provide output signals corresponding therewith; and a retainer assembly abuttably and compressively retaining said crystal detector against said lead assembly at said crystal seating surface, said retainer assembly being formed of electrically conductive material and abuttably coupling electrical ground from said crystal mount to said crystal detector forward face.

32. Probe apparatus for detecting and locating sources of radiation emission, comprising:

a hand supportable housing extending from a rearward end to a forward region, having a wall surmounting an interior handle cavity, said wall having a housing connection region;

a crystal mount, formed of electrically insulative material and supported upon said housing forward region and having a forward portion with an outwardly disposed crystal seating surface and a rearward portion with a rear surface, said crystal mount having a cylindrical outer mount surface of first diametric exten,t said crystal seating surface forming an interior bottom surface of a forwardly opening mount cavity with an interior side surface extending forwardly to a mount cavity edge, and said crystal mount being formed having a retainer groove spaced a predetermined distance inwardly from said mount cavity edge;

a bias conveying and signal receiving lead assembly extending from said crystal seating surface into said handle cavity;

a crystal detector having a rearward face supported upon said crystal seating surface in abutting contact with said bias conveying and signal receiving lead assembly, having a side surface extending to a forward face, and being mounted in closely nesting relationship within said mount cavity, said forward face of said crystal detector being adjacent said mount cavity edge;

a cylindrical sleeve shield formed of material attenuating said radiation, having an open interior surface, surmounting said crystal mount, co-extensive with said crystal detector side surface, and extending to a forward edge;

a window, formed of radiation transmissive material extending over said sleeve shield forward edge;

a treatment circuit located within said handle cavity for applying a bias to said crystal detector rearward face through said lead assembly and applying electrical ground to said crystal detector forward face, and responsive to said detector output to provide output signals corresponding therewith; and a retainer assembly abuttably and compressively retaining said crystal detector against said lead assembly at said crystal seating surface and including an electrically conductive annular ring positioned upon said crystal mount at said mount cavity edge, compressibly retained thereon from said retainer groove, coupled with said electrical ground, and including at least one resilient ground conveying tine in compressive abutting engagement with said crystal detector forward face.

33. Probe apparatus for detecting and locating sources of radiation emission, comprising:

a hand supportable housing extending from a rearward end to a forward region, having a wall surmounting an interior handle cavity, said wall having a housing connection region;

a crystal mount, formed of electrically insulative material and supported upon said housing forward region and having a forward portion with an outwardly disposed crystal seating surface and a rearward portion with a rear surface, said crystal mount having a cylindrical outer mount surface of first diametric extent, said crystal seating surface forming an interior bottom surface of a forwardly opening mount cavity with an interior side surface extending forwardly to a mount cavity edge, and said crystal mount being formed having a retainer groove spaced a predetermined distance inwardly from said mount cavity edge;

a bias conveying and signal receiving lead assembly extending from said crystal seating surface into said handle cavity;

a crystal detector having a rearward face supported upon said crystal seating surface in abutting contact with said bias conveying and signal receiving lead assembly and having a side surface extending to a forward face and being mounted in closely nesting relationship within said mount cavity, said forward face of said crystal being adjacent said mount cavity edge;

a cylindrical sleeve shield formed of material attenuating said radiation, having an open interior surface, surmounting said crystal mount, co-extensive with said crystal detector side surface, and extending to a forward edge;

a window, formed of radiation transmissive material extending over said sleeve shield forward edge;

a treatment circuit located within said handle cavity for applying a bias to said crystal detector rearward face through said lead assembly and applying electrical ground to said crystal detector forward face, and responsive to said detector output to provide output signals corresponding therewith; and a retainer assembly abuttably and compressively retaining said crystal detector against said lead assembly at said crystal seating surface, said retainer assembly including a flat ring formed of resilient metal coupled with said electrical ground positioned upon and coextensive with said mount cavity edge and compressibly retained thereon from said retainer groove, said ring including a plurality of inwardly depending ground conveying tines in compressive abutting engagement with said crystal detector forward face.

34. The probe apparatus of claim 33 in which said annular ring includes at least two resilient integrally formed dogs depending therefrom and in engagement with said retainer groove for compressibly retaining said annular ring upon said crystal mount and conveying said ground.

35. Probe apparatus for detecting and locating sources of radiation emission, comprising:

a hand supportable housing extending from a rearward end to a forward region, having a wall surmounting an interior handle cavity, said wall having a housing connection region;

a crystal mount, formed of electrically insulative material and supported upon said housing forward region and having a forward portion with an outwardly disposed crystal seating surface and a rearward portion with a rear surface, said crystal mount having a cylindrical outer mount surface of first diametric extent;

a bias conveying and signal receiving lead assembly extending from said crystal seating surface into said handle cavity;

a crystal detector having a rearward face supported upon said crystal seating surface in abutting contact with said bias conveying and signal receiving lead assembly and having a side surface extending to a forward face, said forward face of said crystal detector being configured with a surface coating of a given metal;

a cylindrical sleeve shield formed of material attenuating said radiation, having an open interior surface, surmounting said crystal mount, co-extensive with said crystal detector side surface, and extending to a forward edge;

a window, formed of radiation transmissive material extending over said sleeve shield forward edge;

a treatment circuit located within said handle cavity for applying a bias to said crystal detector rearward face through said lead assembly and applying electrical ground to said crystal detector forward face, and responsive to said detector output to provide output signals corresponding therewith; and a retainer assembly abuttably and compressively retaining said crystal detector against said lead assembly at said crystal seating surface, said retainer assembly being configured with a surface coating of said given metal.

36. Probe apparatus for detecting and locating sources of radiation emission, comprising:

a hand supportable housing extending from a rearward end to a forward region, having a wall surmounting an interior handle cavity, said wall having a housing connection region;

a crystal mount, formed of electrically insulative material and supported upon said housing forward region and having a forward portion with an outwardly disposed crystal seating surface and a rearward portion with a rear surface, said crystal mount having a cylindrical outer mount surface of first diametric extent;

a bias conveying and signal receiving lead assembly extending from said crystal seating surface into said handle cavity;

a crystal detector having a rearward face supported upon said crystal seating surface in abutting contact with said bias conveying and signal receiving lead assembly and having a side surface extending to a forward face;

a cylindrical sleeve shield formed of material attenuating said radiation, having an open interior surface, surmounting said crystal mount, co-extensive with said crystal detector side surface, and extending to a forward edge;

a window, formed of radiation transmissive material extending over said sleeve shield forward edge;

a treatment circuit located within said handle cavity for applying a bias to said crystal detector rearward face through said lead assembly and applying electrical ground to said crystal detector forward face, and responsive to said detector output to provide output signals corresponding therewith, said treatment circuit including an integrator stage having components mounted upon a circuit board, and said circuit board is fixed to said crystal mount rearward portion, said components being located in close adjacency with said rearward portion and said channel; and a retainer assembly abuttably and compressively retaining said crystal detector against said lead assembly at said crystal seating surface.

37. The probe apparatus of claim 36 in which said circuit board extends rearwardly outwardly from a rigid mounting with said crystal mount rearward portion within said internal handle cavity.

* * * * *